US007569230B2

(12) United States Patent
Chen et al.

(10) Patent No.: US 7,569,230 B2
(45) Date of Patent: Aug. 4, 2009

(54) STABILIZED FORMULATIONS OF ALPHA ADRENERGIC RECEPTOR ANTAGONISTS AND THE USES THEREOF

(75) Inventors: Andrew X Chen, San Diego, CA (US); Julius Knowles, Del Mar, CA (US); Eckard Weber, San Diego, CA (US)

(73) Assignee: Novalar Pharmaceuticals, Inc., San Diego, CA (US)

( * ) Notice: Subject to any disclaimer, the term of this patent is extended or adjusted under 35 U.S.C. 154(b) by 119 days.

(21) Appl. No.: 11/611,504

(22) Filed: Dec. 15, 2006

(65) Prior Publication Data

US 2007/0098748 A1 May 3, 2007

Related U.S. Application Data

(62) Division of application No. 10/465,810, filed on Jun. 20, 2003, now Pat. No. 7,229,630.

(60) Provisional application No. 60/386,203, filed on Jun. 20, 2002, provisional application No. 60/411,049, filed on Sep. 17, 2002, provisional application No. 60/421,152, filed on Oct. 24, 2002, provisional application No. 60/608,920, filed on Dec. 2, 2002, provisional application No. 60/473,920, filed on May 29, 2003.

(51) Int. Cl.
*A61K 9/08* (2006.01)
*A61K 31/417* (2006.01)
*A61K 31/497* (2006.01)
*A61K 47/12* (2006.01)
*A61K 47/16* (2006.01)
*A61K 47/26* (2006.01)

(52) U.S. Cl. .................. 424/400; 514/252.16; 514/401; 514/818

(58) Field of Classification Search ........................ None
See application file for complete search history.

(56) References Cited

U.S. PATENT DOCUMENTS

| | | | |
|---|---|---|---|
| 4,508,715 A | 4/1985 | Booth et al. | |
| 4,659,714 A | 4/1987 | Watt-Smith | |
| 4,888,344 A | 12/1989 | Sunagawa et al. | |
| 4,938,970 A | 7/1990 | Hustead et al. | |
| 5,149,320 A | 9/1992 | Dhaliwal et al. | |
| 5,192,527 A | 3/1993 | Abrahmsohn | |
| 5,261,903 A | 11/1993 | Dhaliwal et al. | |
| 5,281,591 A * | 1/1994 | Burke .......................... | 514/215 |
| 6,001,845 A | 12/1999 | Estok | |
| 6,025,396 A * | 2/2000 | Kim et al. .................... | 514/573 |
| 6,043,224 A | 3/2000 | Lee et al. | |
| 6,106,866 A | 8/2000 | Ranney | |
| 6,291,498 B1 | 9/2001 | Horn | |
| 6,432,401 B2 * | 8/2002 | Weber et al. ............. | 424/94.62 |
| 6,515,006 B2 | 2/2003 | Horn | |
| 6,764,678 B2 | 7/2004 | Weber et al. | |
| 6,872,390 B2 | 3/2005 | Weber et al. | |
| 2002/0082288 A1 | 6/2002 | Horn | |
| 2004/0176408 A1 | 9/2004 | Horn | |
| 2005/0080056 A1 | 4/2005 | Horn | |
| 2005/0203099 A1 | 9/2005 | Chen et al. | |

FOREIGN PATENT DOCUMENTS

WO      WO 9505188 A1 *  2/1995
WO      WO 01/85171      11/2001

OTHER PUBLICATIONS

U.S. Appl. No. 11/128,184, filed May 2005, Knowles, Julius.*
Kaiser, Fran E, "Erectile Dysfunction" Merck Manuals Online Medical Library, http://www.merck.com/mmhe/sec21/ch240/ch240c.html#sec21-ch240-ch240b-175d, accessed Aug. 18, 2008.*
Ahn, J. and Pogrel, M.A., "The effects of 2% lidocaine with 1:100,000 epinephrine on pulpal and gingival blood flow," *Oral Surg. Oral. Med. Oral. Pathol. Oral. Radiol. Endod.* 85:197-202, Mosby, Inc. (1998).
Alverez, D.J. and Rockwell, P.G., "Trigger Points: Diagnosis and Management," *Am. Fam. Physician* 65:653-660, American Academy of Family Physicians (Feb. 2002).
Bernstein, R.M., and Rassman, W.R., "Limiting epinephrine in large hair transplant sessions," *Hair Transplant Forum International* 10:39-42, New Hair Institute, Inc. (2000), accessed on Aug. 23, 2002 <http://www.800newhair.com/medical_publications/limiting_epinephrine.html>.
Crawford, R.A., et al., "The response of feline spinal pial arterioles to norepinephrine," *J. Neurosurg.* 52:60-63, American Association of Neurological Surgeons (1990).
Edwall, B., et al., "Neuropeptide Y (NPY) and sympathetic control of blood flow in oral mucosa and dental pulp in the cat," *Acta Physiol. Scand.* 125:253-264, Blackwell Scientific Publications (1985).
Hardy, S.J. and Agostini, D.E., "Accidental epinephrine auto-injector-induced digital ischemia reversed by phentolamine digital block," *J. Am. Osteopathic Assoc.* 95:377-378, American Osteopathic Association (1995).
Heasman, P.A. and Jacobs, D.J., "A Clinical Investigation into the Incidence of Dry Socket," *Br. J. Oral Maxillofacial Surg.* 22:115-122, Churchill Livingstone (1984).
Koss, M.C., "Differential neural activation of vascular α-adrenoceptors in oral tissues of cats," *Eur. J. Pharmacol.* 440:53-59, Elsevier Science B.V. (Apr. 2002).
Maguire, W.M., et al., "Epinephrine-Induced Vasospasm Reversed by Phentolamine Digital Block," *Am. J. Emerg. Med.* 8:46-47, W.B. Saunders (1990).
McGovern, S.J., "Treatment of accidental digital injection of adrenaline from an auto-injector device," *J. Accid. Emerg. Med.* 14:379-380, BMJ Publishing Group (1997).

(Continued)

*Primary Examiner*—Johann R Richter
*Assistant Examiner*—Christopher R Lea
(74) *Attorney, Agent, or Firm*—Sterne, Kessler, Goldstein & Fox P.L.L.C.

(57) ABSTRACT

The present invention provides compositions and stable liquid formulations comprising alpha adrenergic receptor antagonists and use thereof for increasing blood flow. In one embodiment, the stable liquid formulations of this invention are useful for reversing the effects of an anesthetic agent, preferably a long-lasting local anesthetic agent administered in conjunction with an alpha adrenergic receptor agonist.

33 Claims, 5 Drawing Sheets

OTHER PUBLICATIONS

Medical Economics, *Physicians' Desk Reference*, Medical Economics Company, Inc., Montvale, NJ, pp. 3135-3137 (Nov. 2001).

Medical Economics, *Physicians' Desk Reference*, Medical Economics Company, Inc., Montvale, NJ, pp. 464, 2668, 2669 and 3268 (Nov. 2001).

Pimentel, L.A.S., and Goldenburg, R.C.D.S., "Local Injection of Hyaluronidase in Increasing Skin Flap Survival: An Experimental Study," *Revista da Sociedade Brasileira de Cirurgia Plastica 14*:49-55, Sociedade Brasileira de Cirurgia Plastica (1999).

Robertson, V.J., et al., "Quantitative and Qualitative Analysis of the Pressor Effects of Levonordefrin," *J. Cardiovasc. Pharmacol. 6*:929-935, Raven Press (1984).

Swinyard, E.A., "Local Anesthetics," in *Remington's Pharmaceutical Sciences*, Osol, A. et al., eds., Mack Publishing Co., Easton, PA, pp. 991-1003 (1980).

Wilson, C.O., and Gisvold, O., eds., *Textbook of Organic Medicinal and Pharmaceutical Chemistry, $2^{nd}$ Edition*, J.B. Lippincott Company, Philadelphia, PA, pp. 25-27 (1954).

International Search Report for International Application No. PCT/US03/19440, mailed Dec. 10, 2003, International Searching Authority, U.S.A.

Office Action for U.S. Appl. No. 11/082,968, Chen, A.X., et al., filed on Mar. 18, 2005, mailed on Sep. 3, 2008.

* cited by examiner

STABILIZED FORMULATIONS OF ALPHA ADRENERGIC RECEPTOR ANTAGONISTS AND THE USES THEREOF

BACKGROUND OF THE INVENTION

1. Field of the Invention

The invention is in the field of pharmaceutical chemistry. The invention relates in particular to a method of reversing local anesthesia induced by a local anesthetic and an alpha-adrenergic agonist, comprising administering an effective low dose of a stabilized liquid formulation of an alpha-adrenergic antagonist.

2. Related Art

Local anesthesia is widely used by dentists to provide pain relief to patients during dental procedures. To provide pain relief, a drug formulation containing a local anesthetic compound such as lidocaine is injected into the gum tissue surrounding the tooth or teeth on which the dental procedure is to be performed. There are short-acting and long-lasting local anesthetic drug formulations. Short-acting local anesthetic drug formulations contain lidocaine or a related local anesthetic drug dissolved in saline or other suitable injection vehicle. Typically, local anesthesia with short-acting local anesthetics lasts approximately 20-30 minutes, which is not long enough for many dental procedures. To obtain long-lasting local anesthesia, dentists often use lidocaine or other local anesthetic formulations which, in addition to the local anesthetic drug itself, contain low concentrations of epinephrine or another adrenergic receptor agonist such as levonordefrin. More than 90% of the local anesthesia procedures performed by dentists involve local anesthetic formulations containing alpha adrenergic receptor agonists. The vasoconstrictor is necessary because local anesthetics without vasoconstrictor are too short-acting for most dental procedures. The added epinephrine stimulates alpha adrenergic receptors on the blood vessels in the injected tissue. This has the effect of constricting the blood vessels in the tissue. The blood vessel constriction causes the local anesthetic to stay in the tissue much longer, resulting in a large increase in the duration of the anesthetic effect (from 20 minutes for the short-acting formulation to 3-6 hours for the long-lasting formulation). A major problem with the use of epinephrine-containing local anesthetics is soft-tissue anesthesia (lip, cheek, tongue) which usually lasts many hours longer than anesthesia and analgesia of the tooth pulp. Tooth pulp anesthesia and analgesia are the desired effects of local anesthesia from a dental procedural perspective while soft-tissue anesthesia is usually an undesirable side effect. Soft tissue anesthesia results in a number of problems and inconveniences, such as a prolonged and uncomfortable feeling of numbness in and around the mouth, inability to smile, difficulty eating, drinking and swallowing, loss of productivity by missing work hours or meetings etc. Lingering soft-tissue anesthesia can be the cause of injuries due to biting of the tongue or lips. Furthermore, lingering soft-tissue anesthesia is an inconvenience and it is perceived as an annoyance by many patients. Lingering soft-tissue anesthesia can lead to injury especially in children who often bite into the anesthetized tissue out of curiosity. It would therefore be desirable to have a drug that could be used at will by dentists to rapidly reverse local anesthesia after it is no longer needed U.S. Pat. No. 4,659,714 discloses a method of prolonging local anesthesia by coadministering a vasoconstrictor, in particular, a vasoconstrictor that acts upon the alpha adrenergic receptor sites of the blood vessel walls. The '714 patent also discloses the subsequent administration of an alpha adrenergic receptor antagonist to cause reduction of the prolonged anesthesia effect. Included within the group of alpha adrenergic receptor antagonists described in this patent are phentolamine mesylate. However, the examples make reference to the administration of "phentolamine." It is much more likely that what was administered was phentolamine mesylate since phentolamine mesylate is FDA approved and readily soluble in water. In contrast, phentolamine is not FDA approved and is relatively insoluble in water.

As shown in Example 1, Table 1 of the '714 patent, 0.5-1.5 mg of "phentolamine" was administered to groups of patients which were pretreated with lignocaine admixed with epinephrine. The results in Table 1 show a reduction in the duration of anesthesia with increasing amounts of "phentolamine." In Example 2, 2 mg of "phentolamine" was administered. In Example 3, four injections of 1 mg each (4 mg total) of "phentolamine" were administered. In Example 4, four injections of 1 mg each (4 mg total) of "phentolamine" were administered.

The drug doses of "phentolamine" described in the '714 patent (0.5-4 mg) overlap the doses of phentolamine mesylate that are approved by the FDA for the systemic treatment of high blood pressure in patients with pheochromocytoma (total dose of 5 mg in a solution of 2.5-5 mg/ml). Since those doses are normally intended for systemic treatment of high blood pressure, those high dose levels can cause severe side effects when used in healthy, normal people. The package insert of the phentolamine mesylate product states the following side effect warning: "Myocardial infarction, cerebrovascular spasm, and cerebrovascular occlusion have been reported to occur following the administration of phentolamine, usually in association with marked hypotensive episodes." Thus, the drug doses taught by the '714 patent for the reversal of local anesthesia may cause unacceptable side effects, precluding the use of this product for anesthesia reversal in healthy normal subjects in a dentist's office.

It has been discovered that a highly effective local anesthesia reversal can be obtained by injections of much lower concentrations of phentolamine mesylate than is disclosed in the '714 patent. See WO 01/85171. It has been found that a solution containing only 0.05 mg/ml of phentolamine mesylate can rapidly reverse the effect of a local anesthetic containing an alpha adrenergic receptor agonist. This phentolamine mesylate drug concentration is 20-100 times lower than the phentolamine mesylate drug concentration taught by the '714 patent. The advantage is that, at such low phentolamine mesylate drug concentrations, no systemic side effects such as myocardial infarction and cerebrovascular spasm will be observed. This allows the safe and effective use of phentolamine mesylate for local anesthesia reversal without causing life-threatening or other untoward side effects. Indeed, in a human clinical efficacy study using a low concentration formulation of phentolamine mesylate, a highly effective anesthesia reversal was observed without any side-effects whatsoever. This constitutes a crucial improvement of the local anesthesia reversal method taught by the '714 patent.

The present invention is directed to the discovery that prior art formulations of phentolamine mesylate are unstable in water and can not be stored reconstituted in water or saline. Stable liquid formulations have also been discovered which allow prolonged storage of phentolamine mesylate.

BRIEF SUMMARY OF THE INVENTION

The present invention provides compositions and stable liquid formulations comprising alpha adrenergic receptor antagonists and use thereof for increasing blood flow. In one embodiment, the stable liquid formulations of this invention are useful for reversing the effects of an anesthetic agent, preferably a long-lasting local anesthetic agent administered in conjunction with an alpha adrenergic receptor agonist.

In one embodiment, the invention relates to a method of increasing blood flow in a mammal, comprising administering to mammal a stable liquid formulation comprising an alpha adrenergic receptor antagonist.

In a preferred embodiment, the administration of a stable liquid formulation comprising an alpha adrenergic receptor antagonist is used to counteract a prior administration of an alpha adrenergic receptor agonist.

In another embodiment, the invention relates to a method of providing local anesthesia to a mammal, comprising:
- (a) administering to the mammal in need thereof an anesthetic agent in an amount effective to provide local anesthesia, and then
- (b) administering a stable liquid formulation comprising an alpha adrenergic receptor antagonist to said site to reduce the time of anesthesia.

In a preferred embodiment, the invention relates to a method of providing local anesthesia to a mammal, comprising:
- (a) administering to the mammal in need thereof an anesthetic agent and an alpha adrenergic receptor agonist to the site to be anesthetized, wherein said anesthetic agent is administered in an amount effective to provide local anesthesia and said alpha adrenergic receptor agonist is administered in an amount effective to constrict the blood vessels at the site and prolong the local anesthesia, and then
- (b) administering a stable liquid formulation comprising an alpha adrenergic receptor antagonist to said site to reduce the prolongation.

In a more preferred embodiment, the invention relates to a method of providing local anesthesia to a human, comprising:
- (a) administering to a human in need thereof by injection to the site to be anesthetized a solution comprising polocaine and levonordefrin, wherein said polocaine is administered in an amount effective to provide local anesthesia and said levonordefrin is administered in an amount effective to constrict the blood vessels at the site and prolong the local anesthesia, thereby producing local anesthesia at said site,
- (b) carrying out a medical procedure on the human, and then
- (c) administering a stable liquid formulation comprising phentolamine mesylate at said site at a concentration of about 0.1 mg/ml or less to reduce the prolongation.

The invention also relates to a method of enhancing the survival of a tissue graft, comprising
- (a) administering to a mammal undergoing a tissue graft an anesthetic agent and an alpha adrenergic receptor agonist to the site of the tissue graft, wherein said anesthetic agent is administered in an amount effective to provide local anesthesia and said alpha adrenergic receptor agonist is administered in an amount effective to constrict the blood vessels at the site and prolong the local anesthesia,
- (b) performing the tissue graft procedure, and then
- (c) administering a stable liquid formulation comprising an alpha adrenergic receptor antagonist to said site to reduce the prolongation and enhance the tissue graft survival.

The invention also relates to a method of reducing the occurrence of dermal necrosis during a medical procedure, comprising
- (a) administering to a mammal undergoing a medical procedure an anesthetic agent and an alpha adrenergic receptor agonist to the site of the procedure, wherein said anesthetic agent is administered in an amount effective to provide local anesthesia and said alpha adrenergic receptor agonist is administered in an amount effective to constrict the blood vessels at the site and prolong the local anesthesia,
- (b) performing the medical procedure, and then
- (c) administering a stable liquid formulation comprising an alpha adrenergic receptor antagonist to said site to reduce the prolongation and reduce the occurrence of dermal necrosis during the procedure.

This invention also relates to a method of treating a trigger point in a mammal, comprising:
- (a) performing a trigger point injection in a mammal having a trigger point, optionally with administration of an anesthetic agent, and
- (b) administering a stable liquid formulation comprising an alpha adrenergic receptor antagonist to said site to increase blood flow to the area of the trigger point and enhance the treatment of the trigger point.

The invention also relates to a method of providing a regional anesthetic block to a mammal, comprising:
- (a) administering to the mammal in need thereof an anesthetic agent and an alpha adrenergic receptor agonist in the site to receive the anesthetic block, wherein said anesthetic agent is administered in an amount effective to provide local anesthesia and said alpha adrenergic receptor agonist is administered in an amount effective to constrict the blood vessels in the site and prolong the anesthetic block, and then
- (b) administering a stable liquid formulation comprising an alpha adrenergic receptor antagonist to said site to reduce the prolongation.

This invention also relates to a method of decreasing the occurrence of dry socket, comprising:
- (a) administering to a mammal undergoing a tooth extraction an anesthetic agent and an alpha adrenergic receptor agonist to the site of the tooth extraction, wherein the anesthetic agent is administered in an amount effective to provide local anesthesia and the alpha adrenergic receptor agonist is administered in an amount effective to constrict the blood vessels at the site and prolong the local anesthesia,
- (b) performing the tooth extraction procedure, and then
- (c) administering a stable liquid formulation comprising an alpha adrenergic receptor antagonist to said site to reduce the prolongation and decrease the occurrence of dry socket.

This invention also relates to a method of enhancing the survival of an injured or diseased tooth in a method, comprising:
- (a) administering to a mammal undergoing repair of an injured tooth or treatment of a diseased tooth an anesthetic agent and an alpha adrenergic receptor agonist to the site of the tooth, wherein the anesthetic agent is administered in an amount effective to provide local anesthesia and the alpha adrenergic receptor agonist is administered in an amount effective to constrict the blood vessels at the site and prolong the local anesthesia,
- (b) performing the repair or treatment procedure, and then
- (c) administering a stable liquid formulation comprising an alpha adrenergic receptor antagonist to said site to reduce the prolongation and enhance the survival of the injured or diseased tooth.

This invention also relates to a method for the treatment of periodontal disease, comprising administering to a mammal having periodontal disease a stable liquid formulation comprising an alpha adrenergic receptor antagonist to said site to increase gingival blood flow and enhance the treatment of the periodontal disease.

The invention also relates to a stable liquid formulation comprising an alpha adrenergic receptor antagonist. The formulation may contain additives such as metal chelators and tonicity modifiers which enhance the stability of the alpha adrenergic receptor antagonist and allow storage of the antagonist for long periods (e.g., greater than 12 months).

The invention also relates to a stable liquid formulation comprising phentolamine mesylate.

The invention also relates to a kit comprising a carrier means having in close confinement therein two or more container means, wherein a first container means comprises an anesthetic agent and optionally an alpha adrenergic receptor agonist and a second container means comprises a stable liquid formulation comprising an alpha adrenergic receptor antagonist.

DETAILED DESCRIPTION OF THE INVENTION

Figure 1:
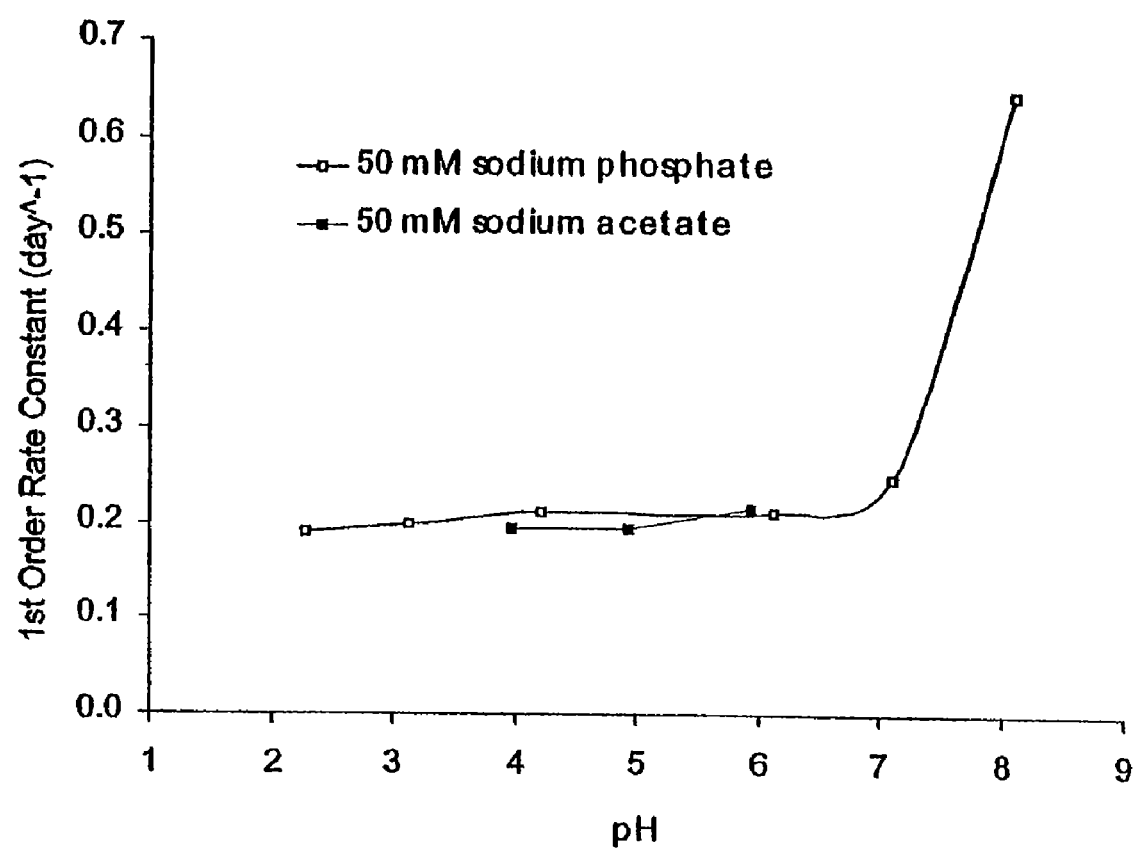
FIG. 1 shows a wide range pH stability profile of phentolamine mesylate at 40° C.

The present invention relates to compositions and stable liquid formulations comprising alpha adrenergic receptor antagonists and use thereof for increasing blood flow. In one embodiment, the invention relates to a method of increasing blood flow in a mammal, comprising administering to the mammal a stable liquid formulation comprising an alpha adrenergic receptor antagonist. In one embodiment of the invention, the increased blood flow is within a specific tissue or portion of the body of the mammal to which the stable liquid formulation has been administered. In another embodiment, the increased blood flow is systemic.

Preferably, the administration of a stable liquid formulation comprising an alpha adrenergic receptor antagonist is used to counteract a prior administration of an alpha adrenergic receptor agonist.

In another embodiment, the invention relates to a method of providing local anesthesia to a mammal, comprising:
(a) administering to the mammal in need thereof an anesthetic agent in an amount effective to provide local anesthesia, and then
(b) administering a stable liquid formulation comprising an alpha adrenergic receptor antagonist to said site to reduce the time of anesthesia.

In a preferred embodiment, the invention relates to a method of providing local anesthesia to a mammal, comprising:
(a) administering to the mammal in need thereof an anesthetic agent and an alpha adrenergic receptor agonist to the site to be anesthetized, wherein said anesthetic agent is administered in an amount effective to provide local anesthesia and said an alpha adrenergic receptor agonist is administered in an amount effective to constrict the blood vessels at the site and prolong the local anesthesia, and then
(b) administering a stable liquid formulation comprising an alpha adrenergic receptor antagonist to said site to reduce the prolongation.

The anesthetic agent and alpha adrenergic receptor agonist may be administered together as part of a unitary pharmaceutical composition or as part of separate pharmaceutical compositions so long as the alpha adrenergic receptor agonist acts to constrict the blood vessels in the vicinity of where the anesthetic agent has been administered to result in a prolonging of anesthesia. In a preferred embodiment, the anesthetic agent and alpha adrenergic receptor agonist are administered together in solution. The anesthetic agent and alpha adrenergic agonist may be administered by injection, by infiltration or by topical administration, e.g. as part of a gel or paste.

In a preferred embodiment, a solution comprising the anesthetic agent and alpha adrenergic receptor agonist is administered by injection directly into the site to be anesthetized, e.g. prior to a dental procedure.

Examples of local anesthetics that may be used in the practice of the invention include without limitation lidocaine, polocaine, lignocaine, xylocaine, novocaine, carbocaine, etidocaine, procaine, prilocaine, bupivacaine, cinchocaine and mepivacaine.

Examples of alpha adrenergic receptor agonists that can be used according to the invention include catecholamines and catecholamine derivatives. Particular examples include without limitation levonordefrin, epinephrine, and norepinephrine.

Examples of alpha adrenergic receptor antagonists that can be used in the practice of the invention include without limitation phentolamine, phentolamine hydrochloride, phentolamine mesylate, tolazoline, yohimbine, rauwolscine, doxazosine, labetalol, prazosine, tetrazosine and trimazosine. Phentolamine mesylate is approved by the FDA for the treatment of hypertension in patients with pheochromocytoma, for the treatment of dermal necrosis and sloughing following accidental extravasation of norepinephrine, and for the diagnosis of pheochromocytoma (phentolamine blocking test). Phentolamine mesylate is supplied as a lyophilized formulation comprising mannitol in vials containing 5 mg of drug substance which may be dissolved in physiological saline or other pharmaceutically acceptable carrier.

In order to reverse the local anesthesia after a medical procedure according to the present invention, the alpha adrenergic receptor antagonist is preferably administered at a low dose, i.e. at a dose that does not cause side effects, i.e. at or below about 0.45 mg per dose for adults (at or below about 0.0064 mg/kg) or 0.18 mg per dose for children, more preferably below about 0.25 mg per dose for adults (at or below about 0.0036 mg/kg) or 0.1 mg per dose for children, more preferably, below about 0.1 mg per dose for adults (below about 0.0014 mg/kg) or 0.04 mg per dose for children, most preferably, at about 0.08 mg per dose for adults (about 0.0011 mg/kg) or about 0.032 mg per dose for children, of phentolamine mesylate or a molar equivalent of another adrenergic receptor antagonist. In a preferred embodiment, the alpha adrenergic receptor antagonist is present at a concentration of about 1 mg/ml or less, preferably from about 0.001 mg/ml to about 0.25 mg/ml, more preferably, about 0.05 mg/ml to about 0.1 mg/ml.

The alpha adrenergic receptor antagonist may be administered by injection into the site of anesthesia, by infiltration or by topical administration. In a preferred embodiment, the alpha adrenergic receptor antagonist is administered to mucosal tissue. In this embodiment, the alpha adrenergic receptor antagonist may be applied to the site in the form of an impregnated wafer, pellet or cotton ball, whereby the antagonist is taken up by the mucosal tissue resulting in reversal of the anesthesia. In another embodiment, the alpha adrenergic receptor antagonist is administered to the site of a regional anesthetic block to reverse the block, e.g. by injection or infiltration into the site. In a preferred embodiment, the alpha adrenergic receptor antagonist is administered via a cannula into the epidural space of an animal to reverse epidural anesthesia.

Examples of medical procedures that may be carried out according to the present invention include, without limitation, both major and minor surgery, dental procedures, cosmetic surgery, tissue grafting (e.g. hair and bone grafting) and cesarean section. In one embodiment, reversal of anesthesia according to the present invention is carried out by medical trainees to mitigate any mistakes that are made, and which may lead to the loss of extremities such as fingers, as well as ears and tips of noses.

Hyaluronidase, an enzyme which enhances the diffusion of drugs within tissues, may be administered together with the alpha adrenergic receptor antagonist. The hyaluronidase and alpha adrenergic receptor antagonist may be administered together as part of a unitary pharmaceutical composition or as part of separate pharmaceutical compositions, so long as the hyaluronidase and alpha adrenergic receptor antagonist are administered to the site where anesthesia is to be reversed and are present in amounts effective to enhance the diffusion of the alpha adrenergic receptor antagonist and to reverse the anesthesia, respectively. The hyaluronidase is administered one or more times into the site of anesthesia. In general, about 1.5 U to about 200 U of hyaluronidase is administered in one or more injections. In a most preferred embodiment, about 200 U of hyaluronidase is administered by injection into the site. Those of ordinary skill in the art can determine optimal amounts of hyaluronidase with no more than routine experimentation.

When performing hair grafts, the surgeon often injects an anesthetic and epinephrine to reduce bleeding and provide a clear vision of the site. According to Bernstein, R. M. and Rassman, W. R., *Hair Transplant Forum International* 10:39-42 (2000), the usefulness of epinephrine in hair graft procedures is limited by a number of factors including post-operative telogen effluvium when epinephrine is used in large transplant sessions. In addition, when adrenaline is added to an area whose blood supply is already compromised by a large number of recipient sites, the tissue may not receive enough oxygen. Although not proven, according to Bernstein and Rassman it is likely that epinephrine infiltration into the recipient area is a contributing factor in the development of the "central necrosis" that has occasionally been reported during hair transplantation. Furthermore, it is possible that the intense vasoconstrictive action of epinephrine may contribute to the decreased graft survival. Thus, according to the present invention, one may achieve enhanced tissue graft survival in a method comprising:

(a) administering to a mammal undergoing a tissue graft an anesthetic agent and an alpha adrenergic receptor agonist to the site of the tissue graft, wherein the anesthetic agent is administered in an amount effective to provide local anesthesia and the alpha adrenergic receptor agonist is administered in an amount effective to constrict the blood vessels at the site and prolong the local anesthesia, (b) performing the tissue graft procedure, and then (c) administering a stable liquid formulation comprising an alpha adrenergic receptor antagonist to said site to reduce the prolongation and enhance the tissue graft survival.

In a preferred embodiment, the tissue graft is a hair graft. In another preferred embodiment, a low dose of alpha adrenergic receptor antagonist is administered to the site to avoid untoward side effects.

Such hair grafts include skin flaps containing a plurality of hair cells and single transplanted hair cell follicles. Typically, such hair grafts are obtained from a site on the animal that has actively growing hair. According to the present invention, an alpha adrenergic receptor antagonist is administered after a hair graft procedure to reverse the local anesthesia and reduce post-operative telogen effluvium (shedding of hair) and survival of the skin flap.

In another embodiment, hyaluronidase may be administered to the tissue graft site to increase survival of the graft. According to Pimentel, L. A. S. and Goldenburg, R. C. d. S, Revista da Soociedade Brasileira de Cirurgia Plastica 14 (1999), the local administration of hyaluronidase increases skin flap survival. According to the authors, hyaluronidase is an enzyme that reduces or prevents tissue injury presumably by causing the rapid diffusion of extravasated fluids to distant areas, thus allowing a better turnover of nutrients. The hyaluronidase is generally injected one or more times into the site of the hair graft. Similarly, the present invention can be used to improve survival of other engrafted tissues or bone in any graft surgical procedure where a local anesthetic and an alpha adrenergic receptor agonist is used to minimize bleeding during the surgery and where subsequent rapid reperfusion of tissue is desired in order to increase graft survival.

In a further preferred embodiment, the tissue graft is a dental implant. According to the present invention, an alpha adrenergic receptor antagonist is administered after a dental implant procedure to reverse the local anesthesia, increase blood flow to the involved area and promote the survival of the implant.

When local anesthesia is used for medical procedures one potential side-effect is dermal necrosis due to the decreased blood flow to the anesthetized area. Rapid reversal of the anesthesia after the procedure is finished would result in increased blood flow and therefore an increased supply of oxygen to the affected tissue. Thus, in an additional embodiment, one may decrease the occurrence of dermal necrosis during a medical procedure in a method comprising:

(a) administering to a mammal undergoing a medical procedure an anesthetic agent and an alpha adrenergic receptor agonist to the site of the procedure, wherein said anesthetic agent is administered in an amount effective to provide local anesthesia and said alpha adrenergic receptor agonist is administered in an amount effective to constrict the blood vessels at the site and prolong the local anesthesia, (b) performing the medical procedure, and then (c) administering a stable liquid formulation comprising an alpha adrenergic receptor antagonist to said site to reduce the prolongation and reduce the occurrence of dermal necrosis during the procedure.

In a preferred embodiment, a low dose of the alpha adrenergic receptor antagonist is administered.

An increasing number of people are carrying and using autoinjectors for emergencies in which rapid treatment of symptoms is necessary. For example, people with severe allergies to bee stings and the like frequently carry an autoinjector containing epinephrine for immediate use when they are stung. The increased use of autoinjectors has led to an increase in the number of accidental needle sticks with the autoinjectors, particularly in the fingertip. Such accidental injection of epinephrine leads to a significant decrease in blood flow to the finger, resulting in tissue necrosis, and, potentially, loss of the finger. Thus, in a further embodiment of the invention, needle sticks with a vasoconstrictor, such as epinephrine, are treated by administering a stable liquid formulation comprising an alpha adrenergic receptor antagonist to the site of the needle stick to reduce the occurrence of tissue necrosis.

Trigger points are discrete, focal, hyperirritable spots located in a taut band of skeletal muscle. Alverez, D. J. and Rockwell, P. G., Amer. Fam. Physician 65:653-660, 2002. Trigger points produce local and referred pain. Needling of the trigger point, either dry or concomitant with injection of a local anesthetic is one of the most effective treatments to inactivate the trigger point and relieve the symptoms. Reperfusion of the trigger point is also thought to provide pain relief. It is therefore advantageous to enhance blood flow to the trigger point during or after injection. Thus, according to the present invention, one may enhance the beneficial effect of trigger point injection in a method comprising:

(a) performing a trigger point injection in a mammal having a trigger point, optionally with administration of an anesthetic agent, and (b) administering a stable liquid formulation comprising an alpha adrenergic receptor antagonist at the site of the trigger point to increase blood flow to the area of the trigger point and enhance the treatment of the trigger point.

When an anesthetic agent is injected into the trigger point, an alpha adrenergic receptor agonist may also be injected in an amount effective to constrict the blood vessels at the site and prolong the local anesthesia. In a preferred embodiment, a low dose of the alpha adrenergic receptor antagonist is administered.

In a further embodiment, a stable liquid formulation of an alpha adrenergic receptor antagonist is administered after a regional anesthetic block to reverse the block. Epidural anesthesia is commonly administered to provide a regional anesthetic block in a number of medical procedures including child birth, cesarean section, surgery to the pelvis and the like. Prolonged epidural anesthesia has many untoward side effects, including prolonged paralysis, inability to voluntarily urinate, and hypotension. Typically, the anesthesiologist injects into the epidural space an equal volume of saline in an effort to dilute the anesthetic and reduce the anesthesia.

The present invention solves the side-effect problems by providing for on demand reversal of the anesthesia without the need for injecting large volumes of saline. In this embodiment, the invention relates to a method of providing a regional anesthetic block to a mammal, comprising:

(a) administering to a mammal in need thereof an anesthetic agent and an alpha adrenergic receptor agonist in the site to receive the anesthetic block, wherein the anesthetic agent is administered in an amount effective to provide local anesthesia and the alpha adrenergic receptor agonist is administered in an amount effective to constrict the blood vessels in the site and prolong the local anesthesia, and then (b) administering a stable liquid formulation of an alpha adrenergic receptor antagonist to the site to reduce the prolongation.

In a preferred embodiment, a low dose of the alpha adrenergic receptor antagonist is administered. In another preferred embodiment, the anesthetic block is epidural anesthesia and the site of the block is the epidural space. The invention has application to reversal of other blocks as well including brachial plexus and femoral blocks.

In another embodiment, hyaluronidase is administered together with the alpha adrenergic receptor antagonist to enhance the diffusion of the alpha adrenergic receptor antagonist within the site of the block, e.g. the epidural space, and speed reversal of the anesthesia.

When a local anesthetic comprising an alpha adrenergic receptor agonist is administered for a dental procedure there is a significant decrease in both gingival and pulpal blood flow which can last for extended periods of time (greater than one hour). Pogrol, A. J., Oral Surg. Oral Med. Oral Pathol. Oral Radiol. Endod. 85:197-202, 1998. Thus, in many dental situations in which blood flow is critical to the continued health of the tooth and/or surrounding tissue, it is advantageous to reverse the effect of the alpha adrenergic receptor agonist as soon as possible after the anesthetic is no longer needed.

When a tooth is extracted, the empty socket fills with blood and a clot is formed. If the clot is prematurely lost or degraded, an extremely painful condition develops due to the exposure of the bone and nerve endings. This condition is known as alveolar osteitis or dry socket. The occurrence of dry socket has been shown to increase when the socket is only partially filled with blood following extraction. Heasman, P. A. and Jacobs, D. J., Br. J. Oral Maxillofacial Surg. 22:115-122, 1984. By reversing local anesthesia after the extraction procedure is completed, blood flow to the area around the extraction socket will increase, leading to enhanced filling of the socket. Thus, according to the present invention, one may decrease the occurrence of dry socket in a method comprising:

(a) administering to a mammal undergoing a tooth extraction an anesthetic agent and an alpha adrenergic receptor agonist to the site of the tooth extraction, wherein the anesthetic agent is administered in an amount effective to provide local anesthesia and the alpha adrenergic receptor agonist is administered in an amount effective to constrict the blood vessels at the site and prolong the local anesthesia, (b) performing the tooth extraction procedure, and then (c) administering a stable liquid formulation comprising an alpha adrenergic receptor antagonist to said site to reduce the prolongation and decrease the occurrence of dry socket.

In a preferred embodiment, a low dose of the alpha adrenergic receptor antagonist is administered.

When traumatic injury to a tooth or tooth disease occurs, necrosis of the pulp tissue can result, often leading to tooth loss. To sustain the vitality of the pulp, blood flow must be maintained and revascularization must occur. By reversing local anesthesia after repair of the injured tooth or treatment of the tooth disease is completed, blood flow to the area of the tooth will increase, leading to enhanced blood flow to the necrotic tissue. Thus, according to the present invention, one may enhance the survival of an injured or diseased tooth in a method comprising:

(a) administering to a mammal undergoing repair of an injured tooth or treatment of a diseased tooth an anesthetic agent and an alpha adrenergic receptor agonist to the site of the tooth, wherein the anesthetic agent is administered in an amount effective to provide local anesthesia and the alpha adrenergic receptor agonist is administered in an amount effective to constrict the blood vessels at the site and prolong the local anesthesia, (b) performing the repair or treatment procedure, and then (c) administering a stable liquid formulation comprising an alpha adrenergic receptor antagonist to said site to reduce the prolongation and enhance the survival of the injured or diseased tooth.

In a preferred embodiment, a low dose of the alpha adrenergic receptor antagonist is administered.

As discussed above, when a local anesthetic comprising an alpha adrenergic receptor agonist is administered for a dental procedure there is a significant decrease in both gingival and pulpal blood flow which can last for extended periods of time (greater than one hour). Under these circumstances, jaw muscles become sore for being open for so long. This soreness is due to the jaw muscles being tired and cramped. Muscle spasm is accentuated by the use of the agonist. The use of an alpha adrenergic antagonist causes rapid localized reperfusion of blood thus reducing or eliminating muscle spasm and post operative pain. In this embodiment, the invention relates to a method of reducing or eliminating muscle spasm or post operative pain, comprising:

(a) administering to a mammal in need thereof an anesthetic agent and an alpha adrenergic receptor agonist in a site to be anesthetized, wherein the anesthetic agent is administered in an amount effective to provide local anesthesia and the alpha adrenergic receptor agonist is administered in an amount effective to constrict the blood vessels in the site and prolong the local anesthesia, and then (b) administering a stable liquid formulation of an alpha adrenergic receptor antagonist to the site to reduce or eliminate muscle spasm or post operative pain at the site.

When the method is to reduce or eliminate post operative pain, a medical procedure (such as a dental procedure) may be performed after (a) and before (b).

The invention also provides for a method of reducing muscle spasm in general such as muscle spasm associated with headache. In this embodiment, an alpha adrenergic receptor antagonist is administered to the site of muscle spasm in an amount effective to reduce or eliminate the muscle spasm. This aspect of the present invention has particular application to the treatment of tension headaches caused by muscle spasm. The alpha adrenergic receptor antagonist may be administered in any way that achieves the intended purpose, e.g. by injection or topical application to the site of muscle spasm.

Periodontal disease is a disease of the gums in which the gums are inflamed and/or bleeding due to the presence of bacteria. Poor gingival blood flow exacerbates periodontal problems. Tobacco smokers have increased periodontal disease, in part due to the fact that smoking decreases gingival blood flow. One of the consequences of periodontal disease is the formation of pockets between the gum and the tooth where the attachment of the gum to the tooth is lost. Treatment of periodontal disease often involves irrigation of periodontal pockets with water and/or medicines to clean and treat the gums. It is advantageous to increase gingival blood flow for the treatment of periodontal disease. Thus, according to the present invention, one may treat periodontal disease in a method comprising administering to a mammal having periodontal disease a stable liquid formulation comprising an alpha adrenergic receptor antagonist at the site of the periodontal disease to increase gingival blood flow, thereby treating the periodontal disease. The alpha adrenergic receptor antagonist can be administered as part of an irrigant for periodontal pockets. In a preferred embodiment, a low dose of the alpha adrenergic receptor antagonist is administered. The alpha adrenergic receptor antagonist can be administered after administration of an anesthetic agent and an alpha adrenergic receptor agonist to the site of the tooth, wherein the anesthetic agent is administered in an amount effective to provide local anesthesia and the alpha adrenergic receptor agonist is administered in an amount effective to constrict the blood vessels at the site and prolong the local anesthesia. The local anesthetic can be administered for a dental procedure related to the periodontal disease, e.g., deep scaling or gum surgery.

The invention also relates to stable liquid formulations comprising alpha adrenergic receptor antagonists, particularly low dose formulations. A "stable liquid formulation" is defined as one in which the alpha adrenergic receptor antagonist is solubilized and wherein the concentration and purity of the alpha adrenergic receptor antagonist is 90% or greater, preferably 95% or greater, after storage at 2-40° C., preferably refrigeration temperature (2-8° C.) or room temperature (25° C.) for at least 3 months, preferably at least 6 months, more preferably at least 12 months.

Examples of alpha adrenergic receptor antagonists that can be used in the stable liquid formulations of this invention include without limitation phentolamine, tolazoline, yohimbine, rauwolscine, doxazosine, labetalol, prazosine, tetrazosine and trimazosine, as well as pharmaceutically acceptable salts of any of the above. In a preferred embodiment, the alpha adrenergic receptor antagonist is a salt of phentolamine. More preferably, the alpha adrenergic receptor antagonist is selected from phentolamine hydrochloride or phentolamine mesylate. Most preferably, the alpha adrenergic receptor antagonist is phentolamine mesylate.

Pharmaceutically acceptable salts of the alpha adrenergic receptor antagonist utilized in the stable liquid formulations of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, mesylate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\ alkyl)_4$ salts. This invention also envisions the quaternization of any basic nitrogen-containing groups of the compounds disclosed herein. Water or oil-soluble or dispersible products may be obtained by such quaternization.

The stable liquid formulation of the present invention may comprise the alpha adrenergic receptor antagonist at any concentration up to the limit of its solubility. This is typically in the range of 0.01 mg/ml to at least 10 mg/ml. In a preferred formulation, the alpha adrenergic receptor antagonist is phentolamine mesylate which is preferably present at a concentration of about 0.01 mg/ml to about 1 mg/ml in the stable liquid formulation, more preferably about 0.01 mg/ml to about 0.25 mg/ml, and most preferably about 0.1 mg/ml to about 0.25 mg/ml. The stable liquid formulation of the invention is preferably present in a container for single dosage administration such that that the total dose of the antagonist, preferably phentolamine mesylate, in the container is between about 0.02 mg to about 0.4 mg. More preferably, the container has between about 0.18 mg and about 0.43 mg of phentolamine mesylate, even more preferably between about 0.40 mg and about 0.43 mg of phentolamine mesylate.

The preferred container for single dosages of the stable liquid formulations of this invention is selected from an ampule, a standard dental cartridge (e.g. a CARPULE) that fits into a standard dental local anesthetic syringe, or a pre-filled syringe. It is further preferred that the container hold a volume of the stable liquid formulations of this invention of between about 1.6 to 1.8 mL. Standard dental cartridges hold up to about 1.8 mL, but the amount of the stable liquid formulation in a dental cartridge according to this invention may vary slightly, depending upon the amount of headspace present after filling the cartridge.

It has now been discovered that stable liquid formulations comprising alpha adrenergic receptor antagonists can be prepared which have a shelf life of at least 12 months at 25° C. The ability to store the antagonist in this fashion is preferable for use in a dental setting or other medical situations, as the formulation is readily available and can be used directly.

In addition to the antagonist, the formulations of this invention comprise a solvent, which may be aqueous or a combination of organic and aqueous and a metal chelator. The formulations of this invention optionally comprise a buffer for maintaining pH, an antioxidant, surfactants, complexing agents and tonicity modifiers.

The solvent used in the formulations of this invention is typically water. In an alternate embodiment, a solvent such as, but not limited to, glycerol, polypropylene glycol, mineral oil or polyethylene glycol is also present. The organic solvent, if present, is preferably at a concentration of between about 5 to 40% (v/v) in water. The preferred solvent is polypropylene glycol. More preferably, polypropylene glycol is present at a concentration of about 25% (v/v) in water.

The presence of a metal chelator is believed to be necessary to maintain stability of the formulation of this invention. The metal chelator is preferably EDTA. When EDTA is employed it is preferably present in the formulation at a concentration of between about 0.5-2.5 mg/ml, more preferably between about 0.5-1.0 mg/ml. Other metal chelators, such as diammonium ethylenediamine triacetate, hydroxyethyl-ethylenediamine triacetic acid, diethylenetriamine pentaacetic acid, nitriloacetic acid, and citric acid may be substituted for EDTA, preferably at an equivalent range of molar concentrations.

The pH of an unbuffered aqueous formulation of this invention is between about 4.0 to 6.0. The stability of the present formulations is not adversely affected at a pH as low as 2.0. Thus according to one embodiment, the stable liquid formulation has a pH in a range of about 2.0 to about 6.0, preferably in a range of about 2.0 to about 5.0, more preferably in a range of about 3.0 to about 4.0, most preferably at about 3.5. In an alternate embodiment, the pH of the formulation is preferably between 3.5 and 4.5, more preferably between 3.8 and 4.2. In order to achieve a pH lower than that produced by simply solubilizing the antagonist in a solvent in the presence of a metal chelator, an acid must be added. In a preferred embodiment, the acid is either acetic acid or methane sulfonic acid. Acidified formulations are preferably buffered with a counter ion which is present in the range of about 1 mM to about 100 mM, preferably about 10 mM to about 50 mM, most preferably about 10 mM. The choice of counter ion is based upon the acid used to lower the pH of the formulation. Thus, when acetic acid is used to lower the pH, the preferred counter ion is sodium acetate. When methane sulfonic acid is used to lower the pH and phentolamine mesylate is the antagonist, the mesylate serves as an appropriate counter ion and no additional counter ion need be added. If the pH of the formulation is too low, NaOH may be added to raise the pH back to the desired level.

Optional tonicity modifiers that may be present in the formulations of this invention include, but are not limited to, NaCl, d-mannitol and dextrose. When present, the tonicity modifier is preferably at a concentration of between about 1 to 10% (w/v). Preferably, the tonicity modifier is d-mannitol. More preferably, the d-mannitol is present at a concentration of between about 4 to 5% (w/v).

Optional antioxidants present in the formulations of this invention include, but are not limited to, ascorbic acid, sodium metabisulfite, butylated hydroxyanisole, and butylated hydroxytoluene. When present, an antioxidant is used at concentrations effective to carry out its intended function. Such concentrations are well known to those of skill in the art of pharmaceutical formulations (see Remington's Pharmaceutical Sciences, A. Osol (ed.), 16th Edition, Mack Publishing Co., Easton, Pa. (1980)).

As an alternative to employing an antioxidant to enhance stability, the stable liquid formulation of this invention may be stored in a container such that a low level of oxygen is present in the headspace of the container. Preferably, the headspace has less than 2% oxygen. The reduced oxygen formulation can be prepared by purging the container with an inert gas, preferably nitrogen. In one embodiment of the invention, the reduced oxygen formulation is prepared by flushing an empty container with an inert gas, filling the container with the stable liquid formulation while continually flushing with the inert gas, and sealing the container. See, e.g., U.S. Pat. No. 6,274,169.

Optional complexing agents, such as $\alpha$-cyclodextrin or niacinamide may also be present in the formulations of this invention. When complexing agents are employed, they are used at concentrations effective to carry out their intended function. Such concentrations are well known to those of skill in the art of pharmaceutical formulations (see Remington's Pharmaceutical Sciences, A. Osol (ed.), 16th Edition, Mack Publishing Co., Easton, Pa. (1980)).

In a preferred embodiment, the formulation comprises a metal chelator (0.1 mg/ml to 10 mg/ml) and a tonicity modifier (1% to 10%). Most preferably, the formulation comprises disodium EDTA as a metal chelator and d-mannitol as a tonicity modifier.

In a preferred embodiment, the stable liquid formulation is selected from the formulations set forth below:

| Ingredient | Formulation A (per mL) | Formulation B (per mL) | Formulation C (per mL) | Formulation D (per mL) | Formulation E (per mL) | Formulation F (per mL) |
|---|---|---|---|---|---|---|
| Phentolamine Mesylate, USP (Reliable Chemical) | 0.222 mg | 0.222 mg | 0.222 mg | 0.222 mg | 0.222 mg | 0.222 mg |
| EDTA Na$_2$, USP | 0.5 mg | 1.0 mg | 0.5 mg | 1.0 mg | 0.5 mg | 1.0 mg |
| D-Mannitol, USP | 50 mg | 50 mg | 50 mg | 50 mg | 50 mg | 50 mg |
| Sodium Acetate, USP | 1.36 mg | 1.36 mg | — | — | — | — |
| Acetic Acid, USP | q.s. to pH 3.8 to 4.2 | q.s. to pH 3.8 to 4.2 | — | — | — | — |
| Methanesulfonic Acid | — | — | — | — | q.s. to pH 3.5 to 4.5 | q.s. to pH 3.5 to 4.5 |
| PPG | | | | | | |
| WFI | q.s. to 1.0 mL | q.s. to 1.0 mL | q.s. to 1.0 mL | q.s. to 1.0 mL | q.s. to 1.0 mL | q.s. to 1.0 mL |

| Ingredient | Formulation G (per mL) | Formulation H (per mL) | Formulation I (per mL) | Formulation J (per mL) | Formulation K (per mL) | Formulation L (per mL) |
|---|---|---|---|---|---|---|
| Phentolamine Mesylate, USP (Reliable Chemical) | 0.222 mg | 0.1 mg | 0.1 mg | 0.1 mg | 0.1 mg | 0.235 mg |
| EDTA Na$_2$, USP | 0.5 mg | 0.5 mg | 0.5 mg | 0.5 mg | 0.5 mg | 0.5 mg |
| D-Mannitol, USP | 50 mg | 50 mg | 50 mg | 44 mg | — | 50 mg |
| Sodium Acetate, USP | | 1.36 mg | 1.36 mg | 1.36 mg | 6.80 mg | 1.36 mg |
| Acetic Acid, USP | | q.s. to pH 3.5 | q.s. to pH 4.0 | q.s. to pH 3.5 | q.s. to pH 3.5 | q.s. to pH 3.8 to 4.2 |
| PPG | 259.5 mg | | | | | |
| WFI | q.s. to 1.0 mL | q.s. to 1.0 mL | q.s. to 1.0 mL | q.s. to 1.0 mL | q.s. to 1.0 mL | q.s. to 1.0 mL |

The term "about" includes the recited number +/−10%. Thus, "about 0.5" means 0.45 to 0.55.

In a further embodiment of the invention, the stable formulation can be prepared as a semi-solid formulation, for example as a gel or paste. A gel or paste can be a one-phase or two-phase system. Two-phase systems can be made from bentonite. One phase systems can be made from synthetic macromolecules (e.g., carbomer, methylcellulose, carboxymethylcellulose, polyvinyl alcohols) or from natural gums (e.g., tragacanth, sodium alginate, gelatin). See Remington's Pharmaceutical Sciences, A. Osol (ed.), 16th Edition, Mack Publishing Co., Easton, Pa. (1980). Typical gel formulations include polyethylene glycol with or without glycerin, polaxomer (15-50%) with or without glycerin, hydroxypropyl cellulose (around 4%) with a high molecular weight polyethylene glycol, propylene carbonate with stearalkonium hectorate or stearalkonium chloride, or colloidal silicone dioxide (2-10%). A typical paste formulation is APHTHASOL, which comprises benzyl alcohol, gelatin, glyceryl monostearate, mineral oil, pectin, petrolatum, and sodium carboxymethylcellulose. All formulations may contain an antimicrobial agent (e.g., benzyl alcohol, EDTA, methyl and propyl paraben). Formulations for oral and dental use may also contain flavoring agents, such as bubble gum or cherry flavoring and sweeteners such as xylitol or sucrose. See, e.g., U.S. Pat. Nos. 6,447,755, 6,355,001, 6,331,291, 6,312,669, 6,159,446, 5,908,612, and 5,670,138.

The invention also relates to a kit comprising a carrier means such as a carton or box having in close confinement therein two or more container means such as dental cartridges or CARPULEs, vials, tubes, jars and the like. A first container means comprises an anesthetic agent and optionally an alpha adrenergic receptor agonist and a second container means comprises a stable liquid formulation comprising a low dose of an alpha adrenergic receptor antagonist. Alternatively, the alpha adrenergic receptor agonist may be present in a separate container means. A further container means may comprise hyaluronidase. Alternatively, the hyaluronidase is in the same container means as the alpha adrenergic receptor antagonist. In a preferred embodiment, the anesthetic agent, alpha adrenergic receptor agonist, alpha adrenergic receptor antagonist and, optionally, the hyaluronidase are present in 1.8 ml dental cartridges (CARPULES) that fit into a standard dental local anesthetic syringe. Such cartridges are available commercially from a variety of suppliers, e.g. Henry Schein, Port Washington, N.Y. In this embodiment, a cartridge containing the local anesthetic and alpha adrenergic receptor agonist is placed into the syringe, and the mixture is injected. The cartridge may then be removed and a second cartridge inserted which contains the alpha adrenergic receptor antagonist and, optionally, the hyaluronidase.

In a further embodiment, the kit comprises a first container means comprises an anesthetic agent and optionally an alpha adrenergic receptor agonist and a second container means comprises a stable liquid formulation comprising phentolamine mesylate. The phentolamine mesylate may be present at any concentration up to the solubility limit of the drug.

The anesthetic agent, vasoconstrictor and, optionally, the hyaluronidase may be present in solution, preferably, a sterile solution, optionally containing salts and buffers, or as part of a gel or paste for topical administration. See U.S. Pat. No. 4,938,970 and Remington's Pharmaceutical Sciences, A. Osol (ed.), 16th Edition, Mack Publishing Co., Easton, Pa. (1980).

Mammals which may be treated according to the present invention include all mammals that may experience the beneficial effects of the present invention. Such mammals include without limitation humans and veterinary mammals such as cattle, pigs, sheep, horses, dogs, and cats. When applied to children and veterinary animals, the prompt reversal of anesthesia inhibits the child or animal from tearing open fresh sutures.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Example 1

Study Rationale and Purpose

Local anesthesia is widely used by dentists to effect anesthesia during dental procedures. Local anesthetics often contain alpha adrenergic receptor agonists to cause vasoconstriction thereby prolonging anesthesia. The vasoconstrictor is necessary because local anesthetics without vasoconstrictor are too short-acting for most dental procedures. On the other hand, in many instances the prolonged local anesthetic effect lasts much longer than required for many dental procedures. It would be desirable to have a drug that could be used at will to rapidly reverse local anesthesia after it is no longer needed. Lingering local anesthesia can be the cause of injuries due to biting of the tongue or lips. Lingering local anesthesia can also result in loss of productivity due to missed work hours. Lastly, lingering local anesthesia is an inconvenience and it is perceived as an annoyance by many patients. The purpose of the present study was to determine whether phentolamine mesylate, an injectable alpha adrenergic receptor agonist, which is FDA approved for the systemic treatment of hypertension in pheochromocytoma patients, rapidly reverses prolonged local anesthesia when injected locally at a very low concentration. The phentolamine mesylate concentration chosen for the present study was so low that it would be expected to lack systemic side-effects such as severe episodes of hypotension that have been described with the high systemic drug doses which are approved by the FDA for the treatment of hypertension in pheochromocytoma patients.

Study Design

The present human subjects study was designed to determine whether injection of a physiological saline solution containing an extremely low concentration of phentolamine mesylate is able to accelerate the reversal of the effects of a previously injected local anesthetic agent containing an alpha adrenergic receptor agonist. An injection of the physiological saline vehicle (without phentolamine mesylate) served as the control. In order to compare the effects of phentolamine mesylate to the vehicle in the same patient, bilateral local anesthesia injections were made into the mouth of the same patient. This was followed by injection of the phentolamine mesylate containing local anesthetic reversal agent (LARA) into one side of the oral cavity, and injection of the saline vehicle (control) solution into the opposite side of the oral cavity. The time to reversal of the local anesthetic effect on both sides was then recorded to determine whether there is a difference between the two sides.

Drugs

The local anesthetic used was 2% polocaine (mepivacaine hydrochloride) with levonordefrin (1:20,000=0.05 mg/ml) (levonordefrin injection, USP) (Astra USA, Inc., Westborough, Mass. 01581). Levonordefrin is a sympathomimetic amine with a pharmacological profile similar to that of epinephrine, but with a lower potency. The local anesthetic reversal agent (LARA) was prepared as follows: A standard vial containing 5 mg of lyophilized phentolamine mesylate for injection, USP (Bedford Laboratories, Bedford, Ohio 44146) was reconstituted with 1 ml of physiological saline using a sterile, disposable 3 ml syringe and a sterile disposable hypodermic needle. After dissolution of the lyophilized powder, 0.5 ml of the phentolamine mesylate solution was withdrawn and injected into a 50 ml vial of physiological saline for injection (USP) by means of a sterile disposable 3 ml syringe and a sterile disposable hypodermic needle. The resulting LARA thus consisted of 0.05 mg/ml phentolamine mesylate in physiological saline.

Methods

Three healthy, male human subjects, age 34-50, volunteered to have local anesthetic injected in the mouth bilaterally under the lip in an easily repeatable location. The exact time of each injection was recorded. The position chosen was above (apical) the prominence of the root of the upper cuspid teeth. This is a common site selected to numb the cuspids, lateral incisors and upper lip. The volume of the local anesthetic injected was 1.7+0.1 ml on each side of the mouth. Twenty minutes after the local anesthetic was injected, each subject was re-injected with 1.6 ml of LARA on one side and 1.6 ml of physiological saline on the opposite side. A different size needle was used for the anesthetic and LARA or saline. A longer needle (1¼") was used for the local anesthetic resulting in more solution being deposited around the infra-orbital nerves. LARA or saline were injected with a shorter needle (½") resulting in less LARA coming into contact with the anesthetic agent around the infra-orbital nerves. After all subjects received anesthetic agent followed by LARA or saline, the subjects were asked to test the intensity of numbness on both sides at the following sites in the mouth and face: teeth, nose, upper lip and gingiva. Numbness of the teeth was tested by biting or grinding. Lip numbness was tested with the touch of the finger or tongue, and nose numbness was tested with the touch of the finger. Gingiva numbness was tested with the blunt end of a wooden cotton swab.

Blinding

Two of the subjects (E and M) were blinded with respect to the side of the mouth where LARA or saline vehicle were injected, i.e. the subjects were not told by the PI which side received LARA and which side received saline vehicle. The third subject (H) was the PI of the study who injected himself. As a consequence, subject H was not blinded with respect to the side at which LARA or saline were injected.

Results

In all three subjects there was a dramatic acceleration of local anesthesia reversal on the side that had been injected with LARA compared to the side that had been injected with saline. No side-effects of any kind were noted in any of the three subjects. In general, feeling to the teeth returned first. TABLE I shows the times at which numbness disappeared and sensations re-appeared in the three subjects at the various sites on both sides of the mouth and face. In the early stages of recovery the subjects reported that it was somewhat difficult to determine which side of the lip was recovering first. In the later stages of recovery, however, the differences between the two sides of the lip were profound and dramatic. In the other parts of the mouth and face, lateral differences were reported to be pronounced even in the very early stages of recovery. The difficulty to sense lateral differences in the lips between the two sides early in the recovery process is thought to be due to the following fact: The labial branches of the infra-orbital nerve decussate at the midline, resulting in a crossover of innervation (and resulting sensation) at the midline of the upper lip.

TABLE I

Subject E - LARA on right hand side (RHS), Vehicle on LHS

| Site of anesthesia | Recovery Time RHS (Minutes) | Recovery Time LHS (Minutes) |
|---|---|---|
| Teeth 80% Recovered | 21 | 85 |
| Teeth Fully Recovered | 28 | 101 |
| Nose | 30 | 143 |
| Lip | 41 | 83 |
| Gingiva | 46 | 141 |

Subject M - LARA on LHS, Vehicle on RHS

| Site of anesthesia | Recovery Time LHS (Minutes) | Recovery Time RHS (Minutes) |
|---|---|---|
| Teeth | 32 | 121 |
| Nose | 40 | 163 |
| Gingiva | 45 | 102 |
| Lip | 36 | 178 |
| All Sensation | 58 | 229 |

Subject H - LARA on RHS, Vehicle on LHS

| Site of anesthesia | Recovery Time RHS (Minutes) | Recovery Time LHS (Minutes) |
|---|---|---|
| Teeth 80% Recovered | 19 | 201 |
| Teeth 100% Recovered | 27 | 218 |
| Gingiva | 42 | 137 |
| Lip | 37 | 226 |
| Nose | 25 | 140 |
| All Sensation | 58 | 263 |

CONCLUSION

LARA had a profoundly faster effect on removing the numbness associated with local anesthesia than using physiological saline. The total amount of phentolamine-mesylate contained in the administered LARA solution was 0.08 mg (1.6 ml of a 0.05 mg/ml solution). This total dose of phentolamine-mesylate is approximately 62 times lower than the 5 mg dose approved by the FDA for systemic treatment of hypertension in pheochromocytoma patients (1 ml of a 5 mg/ml solution) and which can cause severe episodes of hypotension in normal patients. At the extremely low efficacious doses found to be effective in the present study, any systemic side effects, such as those that can occur with the FDA-approved high dose, are likely to be absent. Indeed, in the present study, no side-effects of any kind were noted during or after administration of 0.05 mg/ml phentolamine mesylate.

Example 2

Study Rationale and Purpose

As discussed in Example 1, it is desirable to rapidly reverse local anesthesia after it is no longer needed, for example following completion of a dental procedure. The results in Example 1 indicate that administration of a low dose of an alpha adrenergic receptor antagonist such as phentolamine mesylate can reverse the anesthesia due to administration of a local anesthetic comprising an alpha adrenergic receptor agonist. It would be convenient to have a stable liquid formulation of a low dose of the alpha adrenergic receptor antagonist which could be stored refrigerated or at room temperature and which could be used directly for administration. Unfortunately, prior art phentolamine mesylate formulations are unstable in water and saline. The purpose of the present study was to determine whether a stable liquid formulation comprising phentolamine mesylate could be developed which would provide a shelf life of at least 12 months at 2-8° C. or 25° C.

Study Design

The phentolamine mesylate formulation development was conducted in a tiered approach to define the optimal composition for the drug. At each tier, one of the critical stability-related formulation parameters was evaluated and the optimal condition was selected. The parameters included pH, buffer species, buffer concentration, and additives including antioxidants, metal chelators, surfactants, and complexing agents. At each tier, a temperature-accelerated stability study at 40° C. or 60° C. was performed in order to define the preferred condition for the parameter. Once optimized formulations were identified, real-time (2-8° C. or 25° C.) and accelerated (40° C., 60° C. and 80° C.) stability studies were performed.

Methods

Phentolamine mesylate (99%, Product Number: 36,165-8) was acquired from Aldrich Chemical Company (Milwaukee, Wis.). This material was used for the majority of the studies. Reference standard phentolamine mesylate (Lot I) was acquired from United States Pharmacopoeia (USP) for use in the real-time and accelerated stability studies. Upon receipt, the phentolamine mesylate was stored at room temperature according to the Certificates of Analysis.

The HPLC analytical method for phentolamine mesylate is an isocratic elution method using 20 mM $KH_2PO_4$ in 45% methanol mobile phase at 1 ml/min flow rate and a Synergi Max RP column. The drug is monitored at a detection wavelength of 232 nm.

1. Preparation of Phentolamine Mesylate Test Solution Samples for Stability Evaluation An appropriate amount of phentolamine mesylate was weighed (accurate to 0.1 mg) and added to an aqueous vehicle containing the selected amount of buffer and/or additive to 0.1 mg/ml concentration. At this concentration, phentolamine mesylate is freely soluble at all studied pH values. Tightly sealed glass vials containing the test solutions were placed in an oven at 40° C. or 60° C. All samples were stored in the dark. Aliquots were removed at designated time points for HPLC analysis and pH measurement. All samples were analyzed without dilution.

2. Preparation of Phentolamine Mesylate Standard Solutions for HPLC Analysis

Standard stock solutions were prepared by accurately weighing the appropriate amount (defined in the individual studies) of phentolamine mesylate drug substance (Aldrich Chemical Company) into a volumetric flask, and filling the flask to volume with the solutions specified in each individual experiment procedure. All standard solutions were stored frozen at −20° C. and thawed at room temperature before use.

3. pH Measurement

In conjunction with HPLC analysis, pH was measured. The measurement was performed using the same samples as used for the HPLC analysis. The pH meter was calibrated using pH 4.00 and 7.00 buffer standards prior to each measurement.

Results

The phentolamine mesylate formulation was developed by studying stability according to the following parameters (tiers).

1. Wide-Range pH-Stability Profiling

This study was conducted to define the range of pH (2-3 units) in which phentolamine mesylate would be most stable. Phentolamine mesylate solutions at 0.1 mg/ml concentration were prepared at pH 2, 3, 4, 6, 7, and 8 in 50 mM sodium phosphate and at pH 4, 5, and 6 in 50 mM sodium acetate. The phosphate buffers were prepared by adding phosphoric acid (3.40 ml) to de-ionized (DI) water, adjusting the pH with 2 N NaOH, and bringing the volume to 1 L in a volumetric flask. The acetate buffers were prepared by adding acetic acid (2.95 ml) to water, adjusting the pH value with 2 N NaOH, and bringing the volume to 1 L in a volumetric flask.

Samples were analyzed by HPLC for phentolamine concentration and purity at an initial time point and after two and five days storage at 40° C. Measurements were performed for pH after samples had been analyzed by HPLC.

In all stability studies, glass serum vials with rubber closures and flip-top seals were used for storage of the samples to minimize fluid loss. The weights of samples were measured at the beginning of the experiment, prior to sampling for analysis, and after resealing the vials to monitor for any weight loss due to heating. No significant weight loss was observed.

At each pH, the concentration was divided by the corresponding initial concentration (day 0) to obtain the percent recovery. The percent recovery was plotted against time for calculation of first-order rate kinetics. The slope of each pH line was calculated as the rate constant and plotted against pH to obtain a wide-range pH-stability profile.

A significant increase in rate of degradation was observed at pH above 7 (FIG. 1). At pH values below 7, the profile seems less characteristic, suggesting the necessity for a narrow range pH profile to precisely determine a narrow pH range in which the drug is most stable. The samples prepared in acetate buffers appeared to be more stable than their counterparts in the phosphate buffers.

2. Narrow-Range pH-Stability Profiling

After defining the preferred pH range for phentolamine mesylate, this study was conducted to define the most favorable pH range (within 1 pH unit).

Phentolamine mesylate solutions at 0.1 mg/ml concentration were prepared at pH 2, 2.5, 3, 3.5 or 4 in 50 mM sodium phosphate. The phosphate buffers were prepared as previously described. The samples were analyzed by HPLC for phentolamine concentration and purity at an initial time point and after 2, 7 and 14 days of storage at 60° C. Measurement of sample pH was done after HPLC analysis.

In order to precisely define the most favorable pH, a stronger stressing condition was needed to generate a greater extent of degradation in the lower pH region. For this study, the incubation condition was shifted from 40° C. to 60° C. TABLE II provides the concentration and purity of phentolamine recovered at each time point. Since the extent of degradation after fourteen (14) days was still less than twenty percent (20%) in most samples, zero-order rate kinetics was used for the degradation curves (concentration versus time). The calculated rate constant was plotted against pH to provide the narrow-range pH-stability profile.

Figure 2:
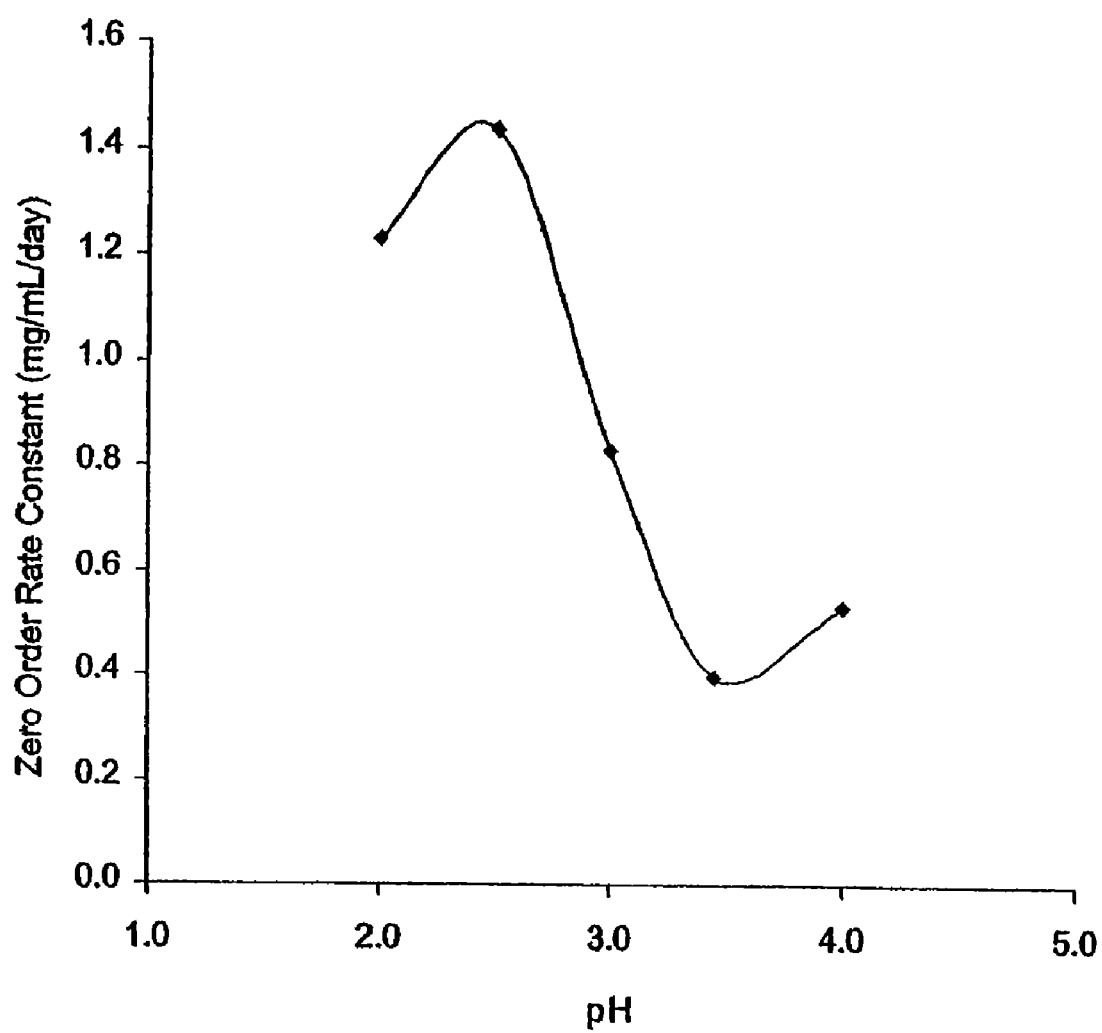
FIG. 2 shows a narrow range pH stability profile of phentolamine mesylate at 60° C.

It was demonstrated that phentolamine was most stable at pH 3.5 (FIG. 2). A narrow-range of the most preferable pH values thus would be defined as pH 3.0 to 4.0 (pH 3.5±0.5).

TABLE II

A Narrow-range pH Stability Profile Study

| Sodium Phosphate Buffer pH | Day 0 | Day 2 | Day 7 | Day 14 |
|---|---|---|---|---|
| Phentolamine Concentration (µg/ml) | | | | |
| pH 2.0 | 98 | 98 | 93 | 81 |
| pH 2.5 | 99 | 96 | 78 | 79 |
| pH 3.0 | 96 | 93 | 91 | 84 |
| pH 3.4 | 97 | 95 | 96 | 91 |
| pH 4.0 | 97 | 95 | 94 | 89 |
| Phentolamine Purity (% peak area) | | | | |
| pH 2.0 | 100 | 99 | 96 | 92 |
| pH 2.5 | 99 | 97 | 92 | 86 |
| pH 3.0 | 99 | 97 | 95 | 91 |
| pH 3.4 | 99 | 98 | 97 | 94 |
| pH 4.0 | 99 | 98 | 97 | 96 |

3. Effect of Buffer Anion on Stability

Having defined the optimal pH range (pH 3 to 4) from the previous two studies, the purpose of this study was to select the most suitable buffer species for buffering phentolamine mesylate solution at the optimal pH value. A comparison of several injectable anionic buffers was made based on the relative stability of phentolamine mesylate under accelerated stability conditions in these buffers. The test buffers included 50 mM sodium phosphate, 50 mM sodium acetate, 50 mM sodium lactate, 50 mM sodium citrate, and 50 mM sodium succinate buffers at pH 3. The 0.1 mg/ml phentolamine mesylate solutions prepared in these buffers were incubated at 60° C. to accelerate the phentolamine mesylate rate of degradation.

The phosphate and acetate buffers were prepared as described above. The citrate buffer was prepared by adding 9.60 g of citric acid to water, adjusting the pH with 2 N NaOH to pH 3, and bringing the volume to 1 L in a volumetric flask. The lactate buffer was prepared by adding 2.25 g of lactic acid to water, adjusting the pH with 2 N NaOH to pH 3, and bringing the volume to 1 L in a volumetric flask. The succinate buffer was prepared by adding 2.95 g succinic acid to water, adjusting the pH with 2 N NaOH to pH 3, and bringing the volume to 1 L in a volumetric flask.

The samples were analyzed by HPLC for phentolamine concentration and purity at one initial time point and after 2, 7 and 14 days of storage at 60° C. Measurements of sample pH were done after HPLC analysis.

TABLE III provides concentration and purity of phentolamine recovered at each time point. Sodium acetate appeared to be the superior buffer. A rank of buffer preference based on the amount of phentolamine recovered at the end of the study may be generated as: sodium acetate>no buffer (water with pH adjusted to pH 3)>sodium phosphate>sodium lactate>sodium succinate>sodium citrate. The strong effect of buffer species on phentolamine stability suggested that degradation of phentolamine is catalyzed by anionic species with the rate of degradation correlated with the negative charge on the anion. A multi-valent anion such as citrate should be avoided. Sodium acetate was selected for further study.

TABLE III

Effect of Anionic Buffer Type on Phentolamine Stability (all sodium salt) at pH 3.0

| Buffer | Day 0 | Day 2 | Day 7 | Day 14 |
|---|---|---|---|---|
| | Phentolamine Concentration (µg/ml) | | | |
| Phosphate | 96 | 93 | 91 | 84 |
| Acetate | 96 | 95 | 94 | 89 |
| Lactate | 97 | 94 | 91 | 83 |
| Citrate | 93 | 87 | 73 | 62 |
| Succinate | 96 | 88 | 74 | 64 |
| | Phentolamine Purity (% peak area) | | | |
| Phosphate | 99 | 97 | 95 | 91 |
| Acetate | 100 | 98 | 97 | 96 |
| Lactate | 99 | 98 | 94 | 89 |
| Citrate | 97 | 91 | 77 | 69 |
| Succinate | 99 | 92 | 78 | 74 |

4. Effect of Buffer Concentration on Stability

After the most suitable buffer species was established (sodium acetate), this study was conducted to determine the optimal buffer concentration based on phentolamine mesylate drug substance stability and stability of the pH (lack of drift) of the solution during storage.

Phentolamine mesylate solutions (0.1 mg/ml) were prepared in sodium acetate buffer at concentrations of 0, 5, 10, and 50 mM at pH 3.5. Samples were incubated at 60° C. with scheduled testing performed at day 0, 2, 7, and 14. The various buffer concentrations were prepared by diluting the 50 mM buffer with water and re-examining the pH value to determine if the pH 3.5 was constant. Measurements of pH were performed after HPLC analysis of the samples.

The concentration and purity of phentolamine recovered from solutions prepared at 0, 5, 10 and 50 mM sodium acetate are provided in TABLE IV. The rate of degradation of phentolamine at 5, 10 and 50 mM sodium acetate appeared to be comparable and was an improvement over the un-buffered control (0 mM). An upward pH drift was observed in all samples, ranging from 0.1 to 0.7 pH units. The pH value was most stable in the 50 mM buffer. While a pH drift beyond the most stable pH range (pH 3.0 to 4.0) would be undesirable, an excessively strong buffer would also be undesirable because a strongly buffered acidic solution may cause tissue irritation or pain at the injection site. Thus, the 10 mM concentration was considered the preferred buffer concentration for the formulation.

TABLE IV

Effect of Buffer Concentration on Stability of Phentolamine Mesylate in Sodium Acetate at pH 3.5

| Buffer Concentration (mM) | Phentolamine Concentration (µg/ml) | | | |
|---|---|---|---|---|
| | Day 0 | Day 2 | Day 7 | Day 14 |
| 50 | 103 | 101 | 99 | 96 |
| 10 | 100 | 97 | 96 | 92 |
| 5 | 99 | 97 | 94 | 92 |
| 0 | 90 | 92 | 82 | 77 |

| Buffer Concentration (mM) | Phentolamine Purity (% peak area) | | | |
|---|---|---|---|---|
| | Day 0 | Day 2 | Day 7 | Day 14 |
| 50 | 98 | 98 | 98 | 96 |
| 10 | 99 | 99 | 98 | 98 |
| 5 | 99 | 99 | 98 | 98 |
| 0 | 99 | 99 | 98 | 97 |

| Buffer Concentration (mM) | pH | | | |
|---|---|---|---|---|
| | Day 0 | Day 2 | Day 7 | Day 14 |
| 50 | 3.5 | 3.6 | 3.6 | 3.6 |
| 10 | 3.5 | 3.7 | 3.8 | 3.7 |
| 5 | 3.5 | 3.8 | 3.8 | 3.8 |
| 0 | 3.6 | 4.4 | 5.1 | 5.3 |

5. Effect of Additives on Stability

After defining the optimal pH, pH buffer species, and pH buffer concentration for a phentolamine mesylate solution, various additives were tested for their potential for enhancing phentolamine stability, and for selection of the most compatible tonicity modifier.

The additives in this study are selected from five groups of injectable excipients namely, tonicity modifiers (NaCl and d-mannitol), metal chelators (EDTA), antioxidants (sodium metabisulfite), complexing agents α-cyclodextrin and niacinamide) and solvents (glycerol and polypropylene glycol). A tonicity modifier is required for adjusting the phentolamine mesylate solution to isotonic. The metal chelator and antioxidant were selected based on the hypothesis that oxidation of phentolamine may occur as suggested by its molecular structure. Complexing agents were applied in the hope that a possible formation of an inclusion complex (by α-cyclodextrin) or stacking complex (by niacinamide) with phentolamine would modify the rate of hydrolytic degradation of the drug substance. Solvents were added to reduce the dielectric constant of the vehicle and were intended to slow the rate of degradation due to solvent polarity.

Solid additives (disodium EDTA, sodium metabisulfite, niacinamide, α-cyclodextrin, mannitol, and sodium chloride) were added directly into the solution of 0.1 mg/ml phentolamine mesylate in 50 mM acetate buffer pH 3.5. The pH value of the solutions was readjusted to pH 3.5, as required. The 25% glycerol (25 g in 100 ml total volume with water) and 25% polypropylene glycol (25 g in 100 ml total volume with water) solutions had their buffer strength adjusted by addition of acetic acid followed by addition of 2 N NaOH for pH adjustment to pH 3.5 followed by addition of the drug to 0.1 mg/ml.

All samples were placed in 10 ml glass serum vials, stoppered with rubber closures with an inert coating (Dalkyo Flurotec by WEST Pharmaceutical), and sealed with flip-top caps after sampling. Vials were placed at 60° C. after the weights were recorded.

Sampling occurred at the initial time point and on days 2, 7, and 14. Vials were weighed, sampled, sealed, re-weighed, and replaced under the selected storage condition until testing at the subsequent time point. Records indicate no significant weight loss during storage.

TABLE V lists the concentration and purity of phentolamine recovered at each time point and the zero-order rate constant. Based on the rate constant and purity value, sodium metabisulfite, NaCl, glycerol, polypropylene glycol and niacinamide were considered undesirable since they had negative impact on the recovery of the phentolamine compared to the no-additive control. The impact of α-cyclodextrin appeared to be negligible based on purity value or perhaps slightly positive based on the rate constant value. At 5% concentration, however, its use in the formulation was determined to be unjustified due to potential toxicity. d-Mannitol and disodium EDTA were found to improve stability based on the rate constant or to exhibit no negative impact based on purity values. Both were selected for inclusion in the formulation, disodium EDTA as stabilizer, d-mannitol as a tonicity modifier.

TABLE V

Effect of Additives on Stability of Phentolamine Mesylate in 10 mM Sodium Acetate, pH 3.5

| Additive | Phentolamine Concentration (μg/ml) | | | | Rate Constant (μg/ml/day) |
|---|---|---|---|---|---|
|  | Day 0 | Day 2 | Day 7 | Day 14 |  |
| EDTA, 0.7 mg/ml | 106 | 103 | 103 | 99 | 0.438 |
| Sodium metabisulfite, 0.5 mg/ml | 97 | 101 | 84 | 74 | 1.903 |
| α-Cyclodextrin, 50 mg/ml | 102 | 99 | 96 | 94 | 0.501 |
| NaCl, 50 mg/ml | 94 | 98 | 80 | 74 | 1.663 |
| Niacinamide, 50 mg/ml | 90 | 90 | 78 | 92 | −0.026 |
| d-Mannitol, 40 mg/ml | 98 | 96 | 98 | 91 | 0.416 |
| Glycerol, 25% w/v | 126 | 123 | 120 | 115 | 0.726 |
| Polypropylene glycol, 25% w/v | 118 | 121 | 113 | 106 | 1.019 |
| No additive | 90 | 92 | 82 | 77 | 1.027 |

| Additive | Phentolamine Purity (% Peak Area) | | | |
|---|---|---|---|---|
|  | Day 0 | Day 2 | Day 7 | Day 14 |
| EDTA, 0.7 mg/ml | 99 | 99 | 99 | 98 |
| Sodium metabisulfite, 0.5 mg/ml | 97 | 99 | 95 | 92 |
| α-Cyclodextran, 50 mg/ml | 98 | 99 | 98 | 98 |
| NaCl, 50 mg/ml | 94 | 99 | 89 | 85 |
| Niacinamide, 50 mg/ml | 99 | 100 | 93 | 90 |
| d-Mannitol, 40 mg/ml | 96 | 97 | 96 | 97 |
| Glycerol, 25% w/v | 98 | 98 | 93 | 94 |
| Polypropylene glycol, 25% w/v | 93 | 97 | 93 | 90 |
| No additive | 99 | 98 | 98 | 97 |

6. Tonicity Testing and Adjustment

Samples were prepared with 2, 3, or 4% w/v d-mannitol with disodium EDTA at 0.5 mg/ml and 0.1 mg/ml phentolamine mesylate in either 10 or 50 mM acetate buffer. A vapor pressure osmometer (Westcore Model 5500) was used to measure the osmolarity of the solutions as well as a control of Normal Saline solution (0.9% sodium chloride, USP). The tonicity of the phentolamine solutions was represented by osmolarity. The measured osmolarity was plotted against d-mannitol concentration. A linear relationship was obtained between the osmolarity and d-mannitol concentration. The concentration of d-mannitol required to achieve the same osmolarity as the Normal Saline solution was calculated for the 10 or 50 mM sodium acetate buffered solution.

TABLE VI lists the osmolarity values for the solutions including Normal Saline (0.9% sodium chloride), which at a measured osmolarity of 292 mmole/kg is considered isotonic to body fluid. The concentration of d-mannitol required to provide isotonicity was calculated to be 4.4% w/v and 5.0% w/v for the 50 mM and 10 mM acetate buffered solutions, respectively.

TABLE VI

Osmolality of 0.1 mg/ml Phentolamine Mesylate with 0.5 mg/ml disodium EDTA in 10 or 50 mM sodium acetate buffer, pH 3.5

| % Mannitol | Measured Osmolality (mmole/Kg) | | Calculated % Mannitol for Isotonicity | |
|---|---|---|---|---|
|  | 10 mM sodium acetate | 50 mM sodium acetate | 10 mM sodium acetate | 50 mM sodium acetate |
| 2 | 176 | 193 | 5.03 | 4.39 |
| 3 | 213 | 234 |  |  |
| 4 | 253 | 276 |  |  |
| Normal Saline | 292 |  |  |  |

7. Real Time and Accelerated Stability Testing

Upon completion of the studies as described above, a final phentolamine mesylate formulation (identified as formulation number 1) was defined as a 0.1 mg/ml phentolamine mesylate solution containing 0.5 mg/ml disodium EDTA, 5.0% w/v d-mannitol in a 10 mM sodium acetate buffer, pH 3.5. Four other formulations (numbers 2, 3, 4 and 5) were identified as listed below. Formulation numbers 2-5 were also included in this study for long-term stability comparisons based on real-time stability data. The real-time stability is a stability profile generated at the preferred storage temperature, i.e. 25° C. or 2-8° C. Stability data generated at elevated temperatures, i.e. 40, 60 and 80° C., could be used to generate an Arrehenius plot in order to predict long-term shelf-life at a lower temperature, as needed. An acceptable shelf-life for a phentolamine mesylate solution formulation is defined as 90-95% recovery of labeled claim of phentolamine mesylate after storage at 25° C. or 2-8° C. for one to two years.

| Formulation | Phentolamine Mesylate | Disodium EDTA | d-mannitol | Sodium acetate | pH |
|---|---|---|---|---|---|
| 1 | 0.1 mg/ml | 0.5 mg/ml | 5% | 10 mM | 3.5 |
| 2 | 0.1 mg/ml | 0.5 mg/ml | 5% | 10 mM | 4.0 |
| 3 | 0.1 mg/ml | 0.5 mg/ml | 4.4% | 50 mM | 3.5 |
| 4 | 0.1 mg/ml | 0.5 mg/ml | 0% | 50 mM | 3.5 |
| 5 | 0.1 mg/ml | 0 mg/ml | 4.4% | 50 mM | 3.5 |

Formulations were prepared aseptically in a laminar flow hood. The solutions were sterilized by filtering through a 0.2-micron sterile filter after the final pH adjustment. All formulations were sterilely filled into vials in a laminar flow hood with a repeat pipettor to transfer 1.5 ml of the filtered solution into 2 ml amber glass vials. Prior to filling, the vials were sterilized and depyrogenated by baking at above 250° C. for approximately sixteen hours. The filled vials were sealed with autoclaved stoppers (13 mm finish gray butyl rubber stopper) and were then capped and weighed prior to placement in stability ovens. All vials were stored in the dark in an upright position. Triplicate vials for HPLC analysis at each time point were prepared and a single HPLC injection for each vial was scheduled. Measurements of pH were to be performed after HPLC analysis of a sample.

Formulation number one vials were placed at −20° C., 2-8° C., 25° C., 40° C., 60° C., and 75-82° C. Formulations 2, 3, 4 and 5 were placed at 25° C. The intended time points for sampling and analysis were up to 48 weeks for the 25° C. samples with truncated sampling schedules for the 40° C., 60° C., and 75-82° C. samples.

During collection of the second week data, it was noted that the frozen standard solution appeared to be less stable than the test samples stored in the liquid state. A decision was made to switch the assay standard from the frozen solution to solid phentolamine mesylate USP standard.

USP reference standard was weighed into each of ten (10) volumetric flasks and stored dry for future use. At each time point, one of these standard aliquots was used to make a standard solution by adding 50 mm acetate buffer, pH 3.5 to the determined volume.

TABLE VII illustrates percentage recovery values of phentolamine concentration at week 1, 2, 3, 4, 8, 12, 24, 36 and 48. For the time 0, week 1 and week 2 values, the phentolamine concentration values were determined by using a separately prepared frozen standard solution. This frozen standard solution was later switched to solid phentolamine USP standard for week 3 samples and later because of an apparent instability observed in the frozen standard solution. Because of this standard switch, an abrupt drop of 1-2% in phentolamine concentration was observed for the samples stored at 40° C. or below.

When a stable standard is used, a typical variation of two percent in concentration is considered normal in HPLC analysis, thus an observed reduction in percentage recovery of less than two percent is not significant. The data in TABLE VII indicate that, at week 3, the total observed reduction in concentration was 4.0, 3.7, 3.8 and 4.7% for the −20° C., 2-8° C., 25° C. and 40° C. stored samples, respectively. The down shift of concentration between week 2 and week 3 due to standard change could account for more than 50% of the total observed reduction in the concentration. Therefore, the loss of concentration in the first 3 weeks is about 2% at most at 40° C. or below. A difference of 2% in concentration could very well be within the HPLC method variation.

From week three to week eight, there appeared to be no loss of concentration of phentolamine in all samples stored at 40° C. or below.

The phentolamine concentration data for the 48-week time point shows 4.6% and 3.2% degradation for samples stored at −20° C. and 2-8° C., respectively. Samples stored at 25° C. showed 6.0% degradation, while samples stored at 40° C. showed 19.9% degradation. The samples stored at 80° C. were completely degraded at the 12-week time point, and samples stored at 60° C. were consumed after 24 weeks.

The concentration recovery values were well supported by the purity values (TABLE VIII). After 8 weeks, the loss of purity was less than two percent for all samples stored at 40° C. or below. The purity data does not accurately reflect the sample purity since it appears that the majority of the degraded material elutes in the column's void volume and is not quantified.

The pH (TABLE IX) of all samples did not change significantly ($\leq 0.2$ pH units) with the exception of the 60° C. and 80° C. stored samples. An upper pH drift of about 0.5 pH unit was observed in the 80° C. stored samples at week 8.

The stability study for formulations 2-5 was only conducted at 25° C. The 48-week concentration data for formulations 2, 3, and 4 show 5.3%, 6.1%, and 4.8% degradation, respectively, similar to that observed for formulation 1. Formulation 5 showed 19.0% degradation. The main difference between formulation 5 and the other four formulations is that formulation 5 does not contain disodium EDTA.

TABLE VII

Real-Time and Accelerated Stability Concentration Data for Phentolamine Formulations

| Formulation | Storage | Time 0 Avg. Conc. (µg/ml)* | Week 1 Avg. Conc. (µg/ml) | Week 2 Avg. Conc. (µg/ml) | Week 3 Avg. Conc. (µg/ml) | Week 4 Avg. Conc. (µg/ml) | Week 8 Avg. Conc. (µg/ml) | Week 12 Avg. Conc. (µg/ml) | Week 24 Avg. Conc. (µg/ml) | Week 36 Avg. Conc. (µg/ml) | Week 48 Avg. Conc. (µg/ml) |
|---|---|---|---|---|---|---|---|---|---|---|---|
| 1 | −20° C. | 101.9 | 100.0 | 100.4 | 97.9 | 98.2 | 99.3 | 98.2 | 96.8 | 98.3 | 97.2 |
| 1 | 2-8° C. | | 100.1 | 101.0 | 98.2 | 98.6 | 100.0 | 98.3 | 97.4 | 99.2 | 98.6 |
| 1 | 25° C. | | 100.9 | 100.3 | 98.1 | 98.2 | 98.7 | 96.8 | 96.8 | 97.3 | 95.8 |
| 1 | 40° C. | | 100.2 | 99.8 | 97.2 | 97.4 | 97.2 | 94.8 | 88.8 | 88.2 | 81.6 |
| 1 | 60° C. | | 100.4 | 98.3 | 94.4 | 94.3 | 90.7 | 82.3 | 69.5 | | |
| 1 | 80° C. | | 91.2 | 76.9 | 58.7 | 54.4 | 4.2 | 0.6 | | | |
| 2 | 25° C. | 100.2 | 99.6 | 98.7 | 96.7 | 97.2 | 98.1 | 95.7 | 94.8 | 96.6 | 94.9 |
| 3 | 25° C. | 102.2 | 102.2 | 101.9 | 98.2 | 99.2 | 99.2 | 97.9 | 96.9 | 95.8 | 96.0 |
| 4 | 25° C. | 102.4 | 102.0 | 101.7 | 95.5 | 99.0 | 99.5 | 98.1 | 97.4 | 95.7 | 97.5 |
| 5 | 25° C. | 101.9 | 99.3 | 96.2 | 94.0 | 94.9 | 93.2 | 89.8 | 89.0 | 85.0 | 82.5 |

*Average of three samples (n = 3)

TABLE VIII

Real-Time and Accelerated Stability Purity Data for Phentolamine Formulations

| Formulation | Storage | Time 0 Purity (% Peak Area)* | Week 1 Purity (% Peak Area) | Week 2 Purity (% Peak Area) | Week 3 Purity (% Peak Area) | Week 4 Purity (% Peak Area) | Week 8 Purity (% Peak Area) | Week 12 Purity (% Peak Area) | Week 24 Purity (% Peak Area) | Week 36 Purity (% Peak Area) | Week 48 Purity (% Peak Area) |
|---|---|---|---|---|---|---|---|---|---|---|---|
| 1 | −20° C. | 99.3 | 99.1 | 99.3 | 99.3 | 99.4 | 99.9 | 98.0 | 98.8 | 98.8 | 98.5 |
| 1 | 2-8° C. |  | 99.4 | 99.2 | 99.2 | 99.4 | 99.2 | 98.3 | 98.6 | 98.7 | 97.8 |
| 1 | 25° C. |  | 99.2 | 99.3 | 99.2 | 99.0 | 99.0 | 98.0 | 98.4 | 98.3 | 97.7 |
| 1 | 40° C. |  | 99.1 | 99.0 | 98.8 | 98.8 | 98.2 | 96.8 | 93.4 | 94.1 | 90.6 |
| 1 | 60° C. |  | 99.5 | 97.8 | 97.5 | 97.4 | 95.6 | 93.2 | 86.8 |  |  |
| 1 | 80° C. |  | 94.9 | 89.5 | 82.4 | 79.7 | 21.6 | 4.4 |  |  |  |
| 2 | 25° C. | 99.2 | 99.1 | 99.1 | 99.1 | 99.1 | 99.0 | 97.9 | 98.1 | 98.1 | 97.4 |
| 3 | 25° C. | 99.1 | 99.0 | 99.1 | 98.8 | 99.1 | 99.1 | 96.9 | 98.3 | 97.4 | 97.6 |
| 4 | 25° C. | 98.7 | 98.5 | 98.7 | 99.0 | 98.7 | 98.4 | 96.7 | 97.7 | 97.2 | 96.6 |
| 5 | 25° C. | 99.4 | 99.2 | 99.2 | 99.1 | 99.2 | 98.8 | 96.5 | 97.0 | 95.2 | 92.4 |

*Average of three samples (n = 3)

TABLE IX

Real-Time and Accelerated Stability pH Data for Phentolamine Formulations

| Formulation | Storage | Time 0 Avg. pH* | Week 1 Avg. pH | Week 2 Avg. pH | Week 3 Avg. pH | Week 4 Avg. pH | Week 8 Avg. pH | Week 12 Avg. pH | Week 24 Avg. pH | Week 36 Avg. pH | Week 48 Avg. pH |
|---|---|---|---|---|---|---|---|---|---|---|---|
| 1 | −20° C. | 3.7 | 3.7 | 3.7 | 3.8 | 3.7 | 3.8 | 3.8 | 3.8 | 3.9 | 3.8 |
| 1 | 2-8° C. |  | 3.7 | 3.7 | 3.8 | 3.7 | 3.8 | 3.7 | 3.8 | 3.8 | 3.7 |
| 1 | 25° C. |  | 3.7 | 3.8 | 3.8 | 3.7 | 3.8 | 3.8 | 3.8 | 3.8 | 3.8 |
| 1 | 40° C. |  | 3.7 | 3.8 | 3.8 | 3.8 | 3.9 | 3.8 | 3.9 | 3.9 | 3.9 |
| 1 | 60° C. |  | 3.8 | 3.8 | 3.9 | 3.8 | 3.9 | 3.9 | 4.0 |  |  |
| 1 | 80° C. |  | 3.8 | 3.9 | 4.0 | 4.0 | 4.2 | 4.3 |  |  |  |
| 2 | 25° C. | 4.3 | 4.3 | 4.3 | 4.3 | 4.3 | 4.4 | 4.4 | 4.4 | 4.3 | 4.4 |
| 3 | 25° C. | 3.7 | 3.7 | 3.7 | 3.7 | 3.7 | 3.7 | 3.7 | 3.8 | 3.7 | 3.7 |
| 4 | 25° C. | 3.7 | 3.7 | 3.7 | 3.7 | 3.7 | 3.8 | 3.8 | 3.8 | 3.8 | 3.8 |
| 5 | 25° C. | 3.6 | 3.6 | 3.6 | 3.6 | 3.6 | 3.6 | 3.7 | 3.7 | 3.6 | 3.7 |

*Average of three samples (n = 3)

Conclusion

The 48-week data show phentolamine mesylate formulations 1-4 to be relatively stable at storage temperatures of 25° C. and lower. The data show that formulation 1 stored at 2-8° C. should remain in specification (i.e., less than 10% loss in concentration and purity) for more than 180 weeks, but has a predicted shelf life, based on the lower 95% confidence limit, of 108 weeks. The data show that formulation 1 stored at 25° C. should remain in specification for 108 weeks, but has a predicted shelf life, based on the lower 95% confidence limit, of 69 weeks. The data show that formulation 2 stored at 25° C. should remain in specification for 103 weeks, but has a predicted shelf life, based on the lower 95% confidence limit, of 63 weeks. The data show that formulation 3 stored at 25° C. should remain in specification for 88 weeks, but has a predicted shelf life, based on the lower 95% confidence limit, of 61 weeks. The data show that formulation 4 stored at 25° C. should remain in specification for 115 weeks, but has a predicted shelf life, based on the lower 95% confidence limit, of 60 weeks.

The rapid degradation of formulation 5 confirms that the presence of disodium EDTA is essential for a stable phentolamine formulation.

Example 3

The objective of this proof-of-principle trial was to evaluate the feasibility of reversing soft-tissue anesthesia by pharmacologically blocking the effects of epinephrine. Twenty healthy adult volunteers were given an inferior alveolar nerve block using one 1.8 ml cartridge of 2% lidocaine with 1:100,000 epinephrine. Sixty minutes later, ten subjects received an injection of phentolamine mesylate for injection, USP (0.2 mg in 1.8 ml), reconstituted and diluted with 0.9% sodium chloride for injection, USP, and 10 other subjects received an injection of saline in the same site as the local anesthetic injection. Subjects self-evaluated the return of normal sensation in their lip, chin, tongue, nose, and teeth by palpations at 5-minute intervals starting at 5 minutes before the study drug injection and continuing for approximately 4-5 hours. To avoid biased responding, subjects were told that they could not leave the clinic for 8 hours after the last injection. Responses for soft tissues were categorized as (1) numb (no feeling), (2) feeling of pins and needles, or (3) normal sensation. Responses for teeth were (1) numb (no feeling) or (2) normal sensation. Safety was evaluated through reports of adverse events, measurement of vital signs and two-lead electrocardiograms before, during, and after the injections of anesthetic and study drug, and through pain assessments using visual analog scales.

Figure 3:
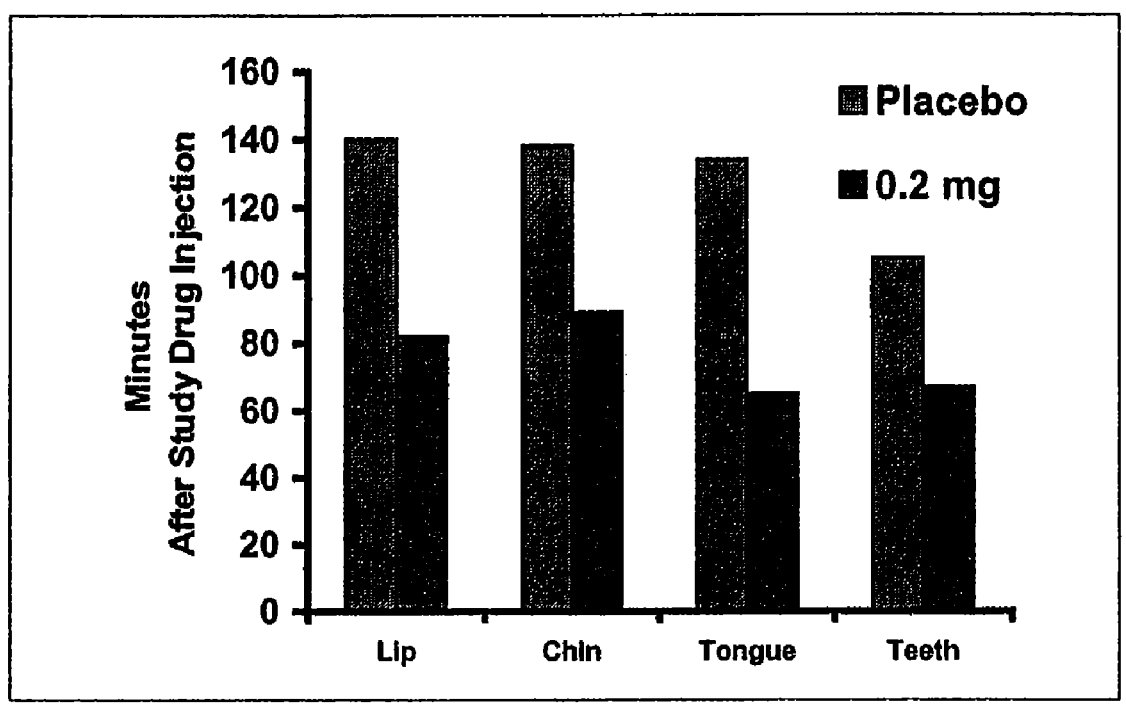
FIG. 3 shows the effect of administration of phentolamine mesylate on the time to return to normal sensation in anesthetized tissues after inferior alveolar nerve block.

Phentolamine mesylate significantly ($p<0.01$) reduced the duration of anesthesia in each tissue. The average times from the injection of study drug until the return to fully normal sensation are depicted in FIG. 3. Adverse effects were few and no differences were noted between the active and placebo groups. There were no abnormalities in the electrocardiogram.

Example 4

The objectives of this study were to evaluate the safety and efficacy of a range of doses of phentolamine in reversing local anesthesia after a mandibular nerve block. Four groups of ten healthy adult volunteer subjects were given an inferior alveolar nerve block using one 1.8 ml cartridge of lidocaine 2% with epinephrine 1:100,000. Sixty minutes later, each group received an injection of phentolamine mesylate for injection, USP (0.02 mg, 0.06 mg, or 0.4 mg in 1.8 ml), reconstituted and diluted with 0.9% sodium chloride for injection, USP, or the saline placebo in the same site as the local anesthetic injection. Subjects palpated their lower lip, chin, tongue, and teeth every five minutes for the next five hours after injections.

Figure 4:
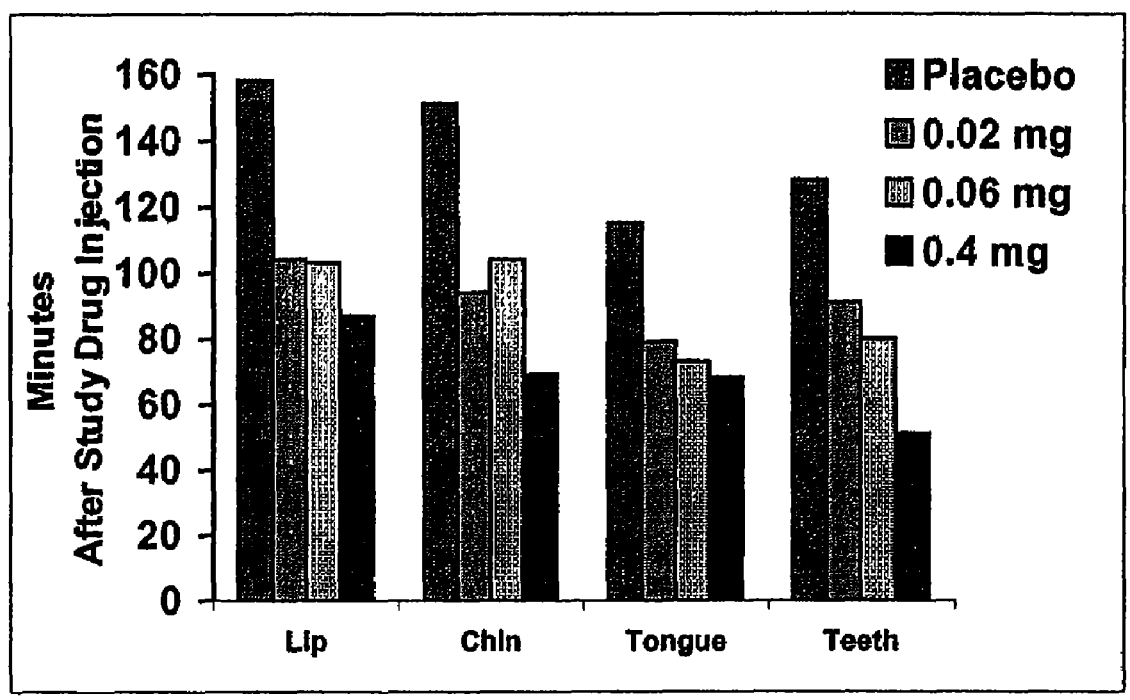
FIG. 4 shows a dose response study of the effect of administration of phentolamine mesylate on the time to return to normal sensation in anesthetized tissues after inferior alveolar nerve block.

Phentolamine mesylate, at all doses tested, significantly ($p<0.05$) reduced the duration of anesthesia in each measured tissue. The average times from the injection of study drug until the return to fully normal sensation are depicted in FIG. 4. Adverse events were few and no differences were noted between the active and placebo groups. There were no abnormalities in the electrocardiogram.

Example 5

The objectives of this study were to evaluate the safety and efficacy of a range of doses of phentolamine in reversing local anesthesia after a maxillary infiltration. Four groups of eight healthy adult volunteer subjects were given an infiltration of the lateral incisor using one 1.8 ml cartridge of lidocaine 2% with epinephrine 1:100,000. Forty minutes later, each group received an injection of phentolamine mesylate for injection, USP (0.02 mg, 0.08 mg, or 0.4 mg in 1.8 ml), reconstituted and diluted with 0.9% sodium chloride for injection, USP, or the saline placebo in the same site as the local anesthetic injection. Subjects palpated their upper lip, nose, and teeth every five minutes for the next five hours after injections.

Figure 5:
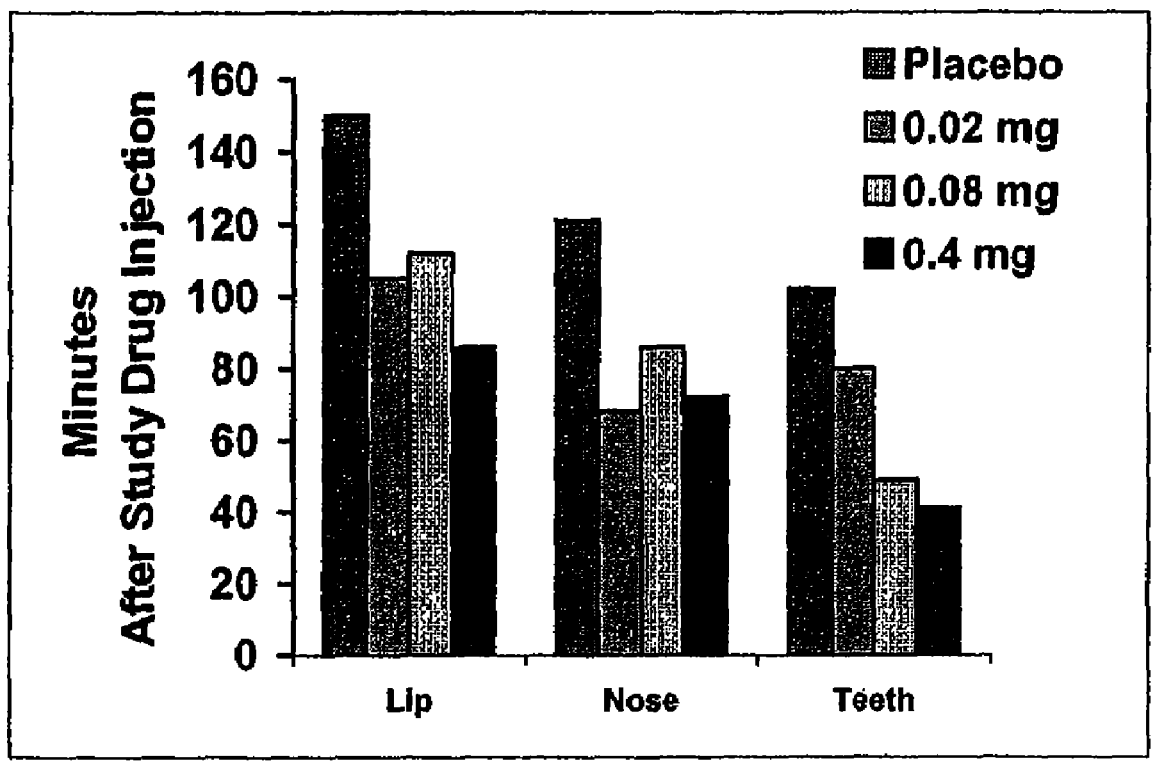
FIG. 5 shows a dose response study of the effect of administration of phentolamine mesylate on the time to return to normal sensation in anesthetized tissues after lateral incisor infiltration.

Phentolamine mesylate, at all doses tested, significantly ($p<0.01$) reduced the duration of anesthesia in each measured tissue. The average times from the injection of study drug until the return to fully normal sensation are depicted in FIG. 5. Adverse events were few and no differences were noted between the active and placebo groups. There were no abnormalities in the electrocardiogram.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A method for increasing blood flow in a mammal comprising administering a stable liquid formulation to said mammal, wherein said stable liquid formulation consists essentially of:
   (a) a low dose of an alpha adrenergic receptor antagonist, a buffer for maintaining pH, an aqueous solvent, a metal chelator, optionally a tonicity modifier, optionally an antioxidant, and optionally a complexing agent, wherein said formulation has a pH of from about 2.0 to about 6.0; or
   (b) an alpha adrenergic receptor antagonist, a buffer for maintaining pH, an aqueous solvent, a metal chelator, optionally a tonicity modifier, optionally an antioxidant, and optionally a complexing agent, wherein said formulation has a pH of from about 2.0 to about 6.0, and wherein said stable liquid formulation is present in a dental cartridge or a pre-filled sterile syringe.

2. The method according to claim 1, wherein said administering a stable liquid formulation counteracts a prior administration to said mammal of an alpha adrenergic receptor agonist.

3. The method according to claim 1, wherein said administering a stable liquid formulation reverses anesthesia caused by prior administration of an anesthetic.

4. The method according to claim 3, wherein said anesthetic was administered with an alpha adrenergic receptor agonist either as a single dosage form or as a separate dosage form.

5. The method according to claim 3, wherein said method is to reverse prolongation of local anesthesia administered as part of a dental procedure.

6. A method according to claim 1, wherein said method is to enhance tissue graft survival, reduce dermal necrosis, decrease dry socket in a mammal undergoing tooth extraction, reduce post-operative pain, reduce muscle spasms, enhance the survival of an injured or diseased tooth, treat a trigger point, reduce the prolongation of a regional anesthetic block or treat periodontal disease.

7. The method according to claim 6, wherein said method is to enhance tissue graft survival and wherein said method further comprises administering hyaluronidase, wherein said hyaluronidase is administered following said tissue graft.

8. The method according to claim 6, wherein said tissue graft is selected from a hair graft, a dental implant or a hair flap.

9. The method according to claim 6, wherein said method is to reduce the prolongation of a regional anesthetic block and comprises administration into the epidural space of said mammal.

10. The method according to claim 6, wherein said method is to treat a periodontal disease and comprises administration as an irrigant for a periodontal pocket.

11. The method according to claim 1, wherein said alpha adrenergic receptor antagonist is selected from the group consisting of phentolamine, phentolamine hydrochloride, phentolamine mesylate, tolazoline, yohimbine, rauwolscine, doxazosine, labetalol, prazosine, tetrazosine, trimazosine, and pharmaceutically acceptable salts thereof.

12. The method according to claim 11, wherein said alpha adrenergic receptor antagonist is phentolamine mesylate.

13. The method according to claim 1, wherein said alpha adrenergic receptor antagonist is present at a concentration of between about 0.01 mg/ml and about 10 mg/ml.

14. The method according to claim 13, wherein said alpha adrenergic receptor antagonist is present at a concentration of between about 0.1 mg/ml and about 0.25 mg/ml.

15. The method according to claim 14, wherein said alpha adrenergic receptor antagonist is phentolamine mesylate.

16. The method according to claim 1, wherein said aqueous solvent is water.

17. The method according to claim 1, wherein said metal chelator is selected from the group consisting of diammonium ethylenediamine triacetate, hydroxyethyl-ethylenediamine triacetic acid, diethylenetriamine pentaacetic acid, nitriloacetic acid, citric acid, and EDTA.

18. The method according to claim 17, wherein said metal chelator is EDTA present at a concentration of between about 0.5 and about 1.0 mg/ml.

19. The method according to claim 18, wherein said alpha adrenergic receptor antagonist is phentolamine mesylate.

20. The method according to claim 1, wherein the pH of said formulation is between about 3.5 and about 4.5.

21. The method according to claim 1, wherein said pH is achieved with a 10 to 50 mM acetate buffer, or with methanesulfonic acid.

22. The method according to claim 21, wherein said alpha adrenergic receptor antagonist is phentolamine mesylate.

23. The method according to claim 1, wherein said stable liquid formulation contains a tonicity modifier.

24. The method according to claim 23, wherein said tonicity modifier is selected from the group consisting of NaCl, d-mannitol, and dextrose.

25. The method according to claim 24, wherein said tonicity modifier is d-mannitol present at a concentration of between about 4 and about 5% (w/v).

26. The method of claim 25, wherein said alpha adrenergic receptor antagonist is phentolamine mesylate.

27. The method according to claim 1, wherein said stable liquid formulation contains an antioxidant in an amount sufficient to prevent oxidization of said alpha adrenergic receptor antagonist.

28. The method according to claim 27, wherein said antioxidant is selected from the group consisting of ascorbic acid, sodium metabisulfite, butylated hydroxyanisole, and butylated hydroxytoluene.

29. The method of claim 28, wherein said alpha adrenergic receptor antagonist is phentolamine mesylate.

30. The method according to claim 1, wherein said stable liquid formulation contains a complexing agent.

31. The method according to claim 30, wherein said complexing agent is selected from the group consisting of α-cyclodextrin, and niacinamide.

32. The method according to claim 31, wherein said alpha adrenergic receptor antagonist is phentolamine mesylate.

33. The method according to claim 1, wherein said alpha adrenergic receptor antagonist is 0.235 mg/ml phentolamine mesylate, said metal chelator is 0.5 mg/ml EDTA, said tonicity modifier is 5% d-mannitol, and said buffer is 16.6 mM acetate buffer, wherein said formulation has a pH of 3.8 to 4.2.

* * * * *